(12) United States Patent
Edge

(10) Patent No.: US 9,896,658 B2
(45) Date of Patent: Feb. 20, 2018

(54) GENERATION OF INNER EAR AUDITORY HAIR CELL

(71) Applicant: Massachusetts Eye & Ear Infirmary, Boston, MA (US)

(72) Inventor: Albert Edge, Brookline, MA (US)

(73) Assignee: Massachusetts Eye & Eat Infirmary, Boston, MA (US)

( * ) Notice: Subject to any disclaimer, the term of this patent is extended or adjusted under 35 U.S.C. 154(b) by 0 days.

(21) Appl. No.: 14/833,919

(22) Filed: Aug. 24, 2015

(65) Prior Publication Data

US 2016/0046906 A1    Feb. 18, 2016

Related U.S. Application Data

(63) Continuation of application No. 13/759,441, filed on Feb. 5, 2013, now abandoned, which is a continuation of application No. 12/233,017, filed on Sep. 18, 2008, now abandoned, which is a continuation of application No. PCT/US2007/084654, filed on Nov. 14, 2007.

(60) Provisional application No. 60/859,041, filed on Nov. 15, 2006.

(51) Int. Cl.
  *C12N 5/071* (2010.01)
  *C12N 5/0793* (2010.01)

(52) U.S. Cl.
  CPC .......... *C12N 5/0627* (2013.01); *C12N 5/062* (2013.01); *C12N 2501/42* (2013.01); *C12N 2506/1353* (2013.01)

(58) Field of Classification Search
  CPC .......... C12N 5/062; C12N 5/0627; C12N 2506/1353; C12N 2501/42; A61K 35/30; A61K 38/1709
  See application file for complete search history.

(56) References Cited

U.S. PATENT DOCUMENTS

| D309,535 S | 7/1990 | Wilson |
| D360,535 S | 7/1995 | Sjoberg |
| D447,031 S | 8/2001 | Oh |
| 6,417,185 B1 | 7/2002 | Goff et al. |
| 6,489,344 B1 | 12/2002 | Nuss et al. |
| 6,608,063 B2 | 8/2003 | Nuss et al. |
| 6,756,511 B2 | 6/2004 | Castro Pineiro et al. |
| 6,890,956 B2 | 5/2005 | Churcher et al. |
| 6,984,626 B2 | 1/2006 | Nadin et al. |
| 7,049,296 B2 | 5/2006 | Castro Pineiro et al. |
| 7,101,895 B2 | 9/2006 | Churcher et al. |
| 7,138,400 B2 | 11/2006 | Collins et al. |
| 7,144,910 B2 | 12/2006 | Madin et al. |
| 7,183,303 B2 | 2/2007 | Castro Pineiro et al. |
| D646,625 S | 10/2011 | Youn |
| 8,188,069 B2 | 5/2012 | Miller et al. |
| 8,617,810 B2 | 12/2013 | Heller et al. |
| 8,673,634 B2 | 3/2014 | Li et al. |
| 2004/0029862 A1 | 2/2004 | Belanger et al. |
| 2004/0049038 A1 | 3/2004 | Collins et al. |
| 2004/0186147 A1 | 9/2004 | Hannam et al. |
| 2005/0019801 A1* | 1/2005 | Rubin ................ G01N 33/5008 435/6.11 |
| 2005/0119293 A1 | 6/2005 | Collins et al. |
| 2005/0143369 A1 | 6/2005 | Castro Pineiro et al. |
| 2005/0182109 A1 | 8/2005 | Collins et al. |
| 2005/0182111 A1 | 8/2005 | Pineiro et al. |
| 2005/0215602 A1 | 9/2005 | Campbell et al. |
| 2005/0287127 A1 | 12/2005 | Li et al. |
| 2008/0267929 A1 | 10/2008 | Li et al. |
| 2009/0098093 A1 | 4/2009 | Edge |
| 2009/0124568 A1 | 5/2009 | Heller et al. |
| 2009/0297533 A1 | 12/2009 | Lichter et al. |
| 2009/0306225 A1 | 12/2009 | Lichter et al. |
| 2011/0020232 A1 | 1/2011 | Eberhart et al. |
| 2011/0033480 A1 | 2/2011 | Sarkar et al. |
| 2011/0305674 A1 | 12/2011 | Edge et al. |
| 2013/0210145 A1 | 8/2013 | Edge |
| 2015/0030568 A1 | 1/2015 | Edge et al. |

FOREIGN PATENT DOCUMENTS

| JP | 2006-117536 | 5/2006 |
| JP | P2006-117536 A * | 5/2006 |
| JP | 2006/520386 | 9/2006 |
| JP | 2007/503816 | 3/2007 |
| JP | 2007/526248 | 9/2007 |
| WO | WO 1998/028268 | 7/1998 |
| WO | 2000/53632 | 9/2000 |
| WO | 2000/59939 | 10/2000 |
| WO | WO 2001/070677 | 9/2001 |
| WO | WO 2002/049038 | 6/2002 |
| WO | WO 2003/093251 | 11/2003 |
| WO | WO 2003/093252 | 11/2003 |
| WO | WO 2003/093253 | 11/2003 |

(Continued)

OTHER PUBLICATIONS

Zheng et al Nature Neuroscience, 2000, 3(6) 580-586.*
Zine et al Development 127, 3373-3383, 2000.*
Geling et al EMBO report, 2002, 688-694.*
Dezawa et al J. Clin. Invest. 113:1701-1710 2004.*
Burton et al Developmental Biology 272 (2004) 161-175.*
Li et al PNAS, 2003, 13495-13500.*
Yamamoto et al Mol Med (2006) 84: 37-45.*
Aletsee et al., "The disintegrin Kistrin inhibits neurite extension from spiral ganglion explants cultured on laminin," Audiol. Neurootol., 6:57-65 (2001).
Artavanis-Tsakonas et al., "Notch Signaling," Sci., 268: 225-232 (1995).
Bartolami et al., "Appearance and Distribution of the 275 kD Hair-Cell Antigen During Development of the Avian Inner Ear," J. Comp. Neurol., 314:777-788 (1991).

(Continued)

*Primary Examiner* — Anoop K Singh
(74) *Attorney, Agent, or Firm* — Fish & Richardson P.C.

(57) ABSTRACT

Methods for generating cells of the inner ear, e.g., hair cells and supporting cells, from stem cells, e.g., mesenchymal stem cells, are provided, as well as compositions including the inner ear cells. Methods for the therapeutic use of the inner ear cells for the treatment of hearing loss are also described.

3 Claims, 10 Drawing Sheets

(56) References Cited

FOREIGN PATENT DOCUMENTS

| WO | WO 2003/093264 | 11/2003 |
|---|---|---|
| WO | WO 2004/039370 | 5/2004 |
| WO | WO 2004/039800 | 5/2004 |
| WO | WO 2005/014553 | 2/2005 |
| WO | WO 2005/030731 | 4/2005 |
| WO | WO 2006/026570 | 3/2006 |
| WO | 2007/075911 | 7/2007 |
| WO | 2008/076556 | 6/2008 |
| WO | WO 2009/087130 | 7/2009 |
| WO | 2010/060088 | 5/2010 |

OTHER PUBLICATIONS

Bouchard et al., "Pax2 and homeodomain proteins cooperatively regulate a 435 bp enhancer of the mouse *Pax5* gene at the midbrain-hindbrain boundary," Develop., 127:1017-28 (2000).

Brors et al., "EphA4 Provides Repulsive Signals to Developing Cochlear Ganglion Neurites Mediated through Ephrin-B2 and -B3," J. Comp. Neurol., 462:90-100 (2003).

Bryant et al., "Sensory organ development in the inner ear: Molecular and cellular mechanisms," British Medical Bulletin, 63:39-57 (2002).

Burton et al., "The role of *Pax2* in mouse inner ear development," Dev. Biol., 272:161-175 (2004).

Cau et al., "*Mash1* activates a cascade of bHLH regulators in olfactory neuron progenitors," Develop., 124:1611-1621 (1997).

Charron et al., "The Morphogen Sonic Hedgehog is an Axonal Chemoattractant that Collaborates with Netrin-1 in Midline Axon Guidance," Cell., 113:11-23 (2003).

Chen et al., "The role of Math1 in inner ear development: Uncoupling the establishment of the sensory primordium from hair cell fate determination," Develop., 129:2495-2505 (2002).

Colter et al., "Rapid expansion of recycling stem cells in cultures of plastic-adherent cells from human bone marrow," Proc. Natl. Acad. Sci. U.S.A , 97:3213-3218 (2000).

Communication issued in EP07871464.9 dated May 6, 2014 (5 pages).

Corrales et al., "Engraftment and Differentiation of Embryonic Stem Cell-Derived Neural Progenitor Cells in the Cochlear Nerve Trunk: Growth of Processes into the Organ of Corti," J. Neurobiol., 66:1489-500 (2006).

Cosgrove et al., Am. J. Pathol., 157:1649-59 (2000).

Declaration of Non-Establishment of International Search Report for PCT/US2009/065747, dated Apr. 8, 2010.

Dezawa et al., "Specific induction of neuronal cells from bone marrow stromal cells and application for autologous transplantation," J. Clin. Invest., 113:1701-1710 (2004).

Doyonnas et al., "Hematopoietic contribution to skeletal muscle regeneration by myelomonocytic precursors," Proc. Natl. Acad. Sci. U.S.A, 101:13507-13512 (2004).

Edge et al., "Current Applications of Cellular Xenografts," Trans. Proc., 32:1169-1171 (2000).

Examination Report issued in Australian Patent Application No. 2007334260 dated Aug. 23, 2012.

Extended European Search Report issued in corresponding European Patent Application No. 07871464.9, dated Nov. 17, 2010.

Extended European Search Report issued in EP 0982830, dated Dec. 7, 2012.

Final Office Action issued in U.S. Appl. No. 13/130,607 dated Oct. 21, 2013.

Fred Gage, Nature, 392:18-24 (1998).

Fritzsch et al., "*Atoh1* Null Mice Show Directed Afferent Fiber Growth to Undifferentiated Ear Sensory Epithelia Followed by Incomplete Fiber Retention," Dev. Dyn., 233:570-583 (2005).

Fritzsch et al., "Lack of Neurotrophin 3 Causes Losses of Both Classes of Spiral Ganglion Neurons in the Cochlea in a Region-Specific Fashion," J. Neurosci., 17:6213-6225 (1997).

Gelling et al., "A gamma-secretase inhibitor blocks Notch signaling in vivo and causes a severe neurogenic phenotype in zebrafish," EMBO Report, 688-694 (2002).

Gillespie et al., "LIF is more potent than BDNF in promoting neurite outgrowth of mammalian auditory neurons in vitro," Neuro. Rep., 12:275-279 (2001).

Gowan et al., "Crossinhibitory Activities of Ngn1 and Math1 Allow Specification of Distinct Dorsal Interneurons," Neuron., 31:219-232 (2001).

Hawkins et al., "The developmental genetics of auditory hair cells," Hum. Mol. Genet., 13:R289-296 (2004).

Heller et al., "Parvalbumin 3 is an Abundant $Ca^{2+}$ Buffer in Hair Cells," J. Assoc. Res. Otolaryngol., 3:488-498 (2002).

Helms et al., "Autoregulation and multiple enhancers control *Math1* expression in the developing nervous system," Develop., 127:1185-1196 (2000).

Helms et al., "Overexpression of MATH1 Disrupts the Coordination of Neural Differentiation in Cerebellum Development," Mol. Cell. Neurosci., 17:671-682 (2001).

Hermann et al., "Efficient generation of neural stem cell-like cells from adult human bone marrow stromal cells," J. Cell. Sci., 117:4411-4422 (2004).

Herzog et al., "Plasticity of marrow-derived stem cells," Blood, 102:3483-3493 (2003).

Hess et al., "Bone marrow-derived stem cells initiate pancreatic regeneration," Nat. Biotechnol., 21:763-770 (2003).

Hu et al., "Survival and neural differentiation of adult neural stem cells transplanted into the mature inner ear," Exper. Cell. Res., 302:40-47 (2005).

Hu et al., Stem Cell and Development, 15:449-459 (2006).

Huawei et al., "Generation of hair cells by stepwise differentiation of embryonic stem cells," Proc. Natl. Acad. Sci. U.S.A., 23:13495-13500 (2003).

International Preliminary Report on Patentability for PCT/US2009/065747, dated May 24, 2011.

International Preliminary Report on Patentability issued in corresponding International Application No. PCT/US2007/084654, dated May 28, 2009.

International Search Report issued in corresponding International Application No. PCT/US2007/84654, dated Oct. 3, 2008.

Ito et al., "Neurotrophins Facilitate Neuronal Differentiation of Cultured Neural Stem Cells Via Induction of mRNA Expression of Basic Helix-Loop-Helix Transcription Factors Mash1 and Math1," J. Neurosci. Res., 71:648-658 (2003).

Ivanov et al., "Genes required for *Drosophila* nervous system development identified by RNA interference," Proc. Nat. Acad. Sci., 101:16216-16221 (2004).

Izumikawa et al., "Auditory hair cell replacement and hearing improvement by Atoh1 gene therapy in deaf mammals," Natl. Med., 11(3):271-276 (Mar. 2005).

Jeon et al., "Bone marrow mesenchymal stem cells are progenitors in vitro for inner ear hair cells," Molecular and Cellular Neurosciences, 34:59-68 (2007).

Jiang et al., "Neuroectodermal differentiation from mouse multipotent adult progenitor cells," Proc. Natl. Acad. Sci .U.S.A, 100:11854-11860 (2003).

Jiang et al., "Pluripotency of mesenchymal stem cells derived from adult marrow," Nature, 418:41-49 (2002).

Kicic et al., "Differentiation of Marrow Stromal Cells into Photoreceptors in the Rat Eye," J. Neurosci., 23:7742-7749 (2003).

Kiernan et al., "*Sox2* is required for sensory organ development in the mammalian inner ear," Nature, 434:1031-1035 (2005).

Kim et al., "Dopamine neurons derived from embryonic stem cells function in an animal model of Parkinson's disease," Nature, 418:50-6 (2002).

Kim et al., "NeuroD-null mice are deaf due to a severe loss of the inner ear sensory neurons during development," Develop., 128:417-426 (2001).

Kondo et al., "Sonic Hedgehog and retinoic acid synergistically promote sensory fate specification from bone marrow-derived pluripotent stem cells," Proc. Natl. Acad. Sci. U.S.A., 102(13):4789-4794 (Mar. 2005).

(56) References Cited

OTHER PUBLICATIONS

Lanford et al., "Notch signalling pathway mediates hair cell development in mammalian cochlea," Nature Genetics, 21:289-292 (1999).
Lang et al., "Contribution of Bone Marrow Hematopoietic Stem Cells to Adult Mouse Inner Ear: Mesenchymal Cells and Fibrocytes," J .Comp. Neurol., 496:187-201 (2006).
Lee et al., "Efficient generation of midbrain and hindbrain neurons from mouse embryonic stem cells," Nat. Biotech., 18:675-9, (2000).
Leon et al.,. "Insulin-Like Growth Factor-I Regulates Cell Proliferation in the Developing Inner Ear, Activating Glycosyl-Phosphatidylinositol Hydrolysis and Fos Expression," Endocrinol., 136:3494-3503 (1995).
Li et al., "Correlation of Pax-2 Expression with Cell Proliferation in the Developing Chicken Inner Ear," J. Neurobiol., 60:61-70 (2004).
Li et al., "Generation of hair cells by stepwise differentiation of embryonic stem cells," Proc. Natl. Acad. Sci U.S.A., 100:13495-13500 (2003).
Li et al., "Pluripotent stem cells from the adult mouse inner ear," Nature Medicine, 9:1293-1299 (2003).
Li et al., "Specification of motoneurons from human embryonic stem cells," Nat. Biotechnol., 23:215-21 (2005).
Li et al., "Stem cells as therapy for hearing loss," Trends Mol. Med., 10:309-315 (2004).
Lu et al., "The Influence of Glycogen Synthase Kinase 3 in Limiting Cell Addition in the Mammalian Ear," Develop. Neurobiol., 68:1059-1075 (2008).
Lumpkin et al., "Math1-driven GFP expression in the developing nervous system of transgenic mice," Gene. Expr. Patterns, 3:389-395 (2003).
Ma et al., "Neurogenin 1 Null Mutant Ears Develop Fewer, Morphologically Normal Hair Cells in Smaller Sensory Epithelia Devoid of Innervation," Assoc. Res. Otolarnyngol., 1:129-143 (2000).
Mangi et al., "Mesenchymal stem cells modified with Akt prevent remodeling and restore performance of infarcted hearts," Nat. Med., 9:1195-201 (2003).
Matei et al., "Smaller Inner Ear Sensory Epithelia in Neurog1 Null Mice Are Related to Earlier Hair Cell Cycle Exit," Dev. Dyn., 234:633-50 (2005).
Matsui et al., Drug Discov. Today, 10:1307-12 (2005).
Mezey et al., "Transplanted bone marrow generates new neurons in human brains," Proc. Natl. Acad. Sci. U.S.A., 100:1364-1369 (2003).
Murry et al., "Haematopoietic stem cells do not transdifferentiate into cardiac myocytes in myocardial infarcts," Nature., 428:664-668 (2004).
Naito Yasushi et al., "Transplantation of bone marrow stromal cells into the cochlea of chinchillas," NeuroReport, Lippincott Williams & Wilkins, 15:1-4 (2004).
Non-Final Office Action issued in U.S. Appl. No. 13/130,607 dated Apr. 19, 2013.
Non-Final Office Action issued in U.S. Appl. No. 13/130,607 dated Oct. 23, 2014.
Office Action issued in Australian Patent Application No. 2009316264 dated Jan. 16, 2015 (5 pages).
Office Action issued in CA2,669,693 dated Apr. 4, 2014 (4 pages).
Office Action issued in European Application No. 09828380.7 dated Mar. 26, 2014 (6 pages).
Office Action issued in Japanese Application No. 2011-537715 dated Feb. 4, 2014 (translation) 4 pages.
Office Action issued in Japanese Patent Application No. 2011-537715 dated Jan. 20, 2015 with English translation (7 pages).
Office Action issued in JP2009-537328 dated Feb. 12, 2013 (7 pages).
Oshima et al., "Differential Distribution of Stem Cells in the Auditory and Vestibular Organs of the Inner Ear," J. Assoc. Res .Otolaryngol., 8:18-31 (2007).

Pagani et al., "Autologous Skeletal Myoblasts Transplanted to Ischemia-Damaged Myocardium in Humans," J. Am. Coll. Cardiol., 41:879-888 (2003).
Patzel et al., "Design of siRNAs producing unstructured guide-RNAs results in improved RNA interference efficiency," Nature Biotechnol., 23:1440-1444 (2005).
Pauley et al., "Expression and Function of FGF10 in Mammalian Inner Ear Development," Dev. Dyn., 227:203-215 (2003).
Pedersen, "Cells for Medicine," Scientif. Am., 280:68-73 (1999).
Petit et al., Annu Rev Genomics Hum Genet., 2:271-97 (2001).
Pirvola et al., "Neurotrophic Factors during Inner Ear Development," Curr. Top. Dev. Biol., 57:207-223 (2003).
Pittenger et al., "Multilineage Potential of Adult Human Mesenchymal Stem Cells," Sci., 284:143-147 (1999).
Plum et al., Dev Biol., 231:334-47 (2001).
Presente et al., "Notch is required for long-term memory in *Drosophila*," Proc. Nat. Acad. Sci., 101:1764-1768 (2004).
Purow et al., "Expression of Notch-1 and Its Ligands, Delta-Like-1 and Jagged-1, Is Critical for Glioma Cell Survival and Proliferation," Cancer Res., 65:2353-2363 (2005).
Rask-Andersen et al., "Regeneration of human auditory nerve. In vitro/in video demonstration of neural progenitor cells in adult human and guinea pig spiral ganglion," Hear. Res., 203:180-191 (2005).
RCE and Response to Final Office Action issued in U.S. Appl. No. 13/130,607, filed Apr. 21, 2014.
Response to Non-Final Office Action issued in U.S. Appl. No. 13/130,607, filed Jul. 19, 2013.
Response to Non-Final Office Action issued in U.S. Appl. No. 13/130,607 dated Oct. 23, 2014 filed Apr. 23, 2015 (10 pages).
Response to Restriction Requirement issued in U.S. Appl. No. 13/130,607, filed Dec. 12, 2012.
Restriction Requirement issued in U.S. Appl. No. 13/130,607 dated Oct. 12, 2012.
Sakamoto et al., Acta Otolarynol Suppl., 551:48-52 (2004).
Samstein et al., Journal of American Society of Nephrology, 12:182-193 (2001).
Sarrazin et al., "Proneural gene requirement for hair cell differentiation in the zebrafish lateral line," Dev. Biol., 295:534-545 (2006).
Satoh and Fekete, "Clonal analysis of the relationships between mechanosensory cells and the neurons that innervate them in the chicken ear," Develop., 132:1687-1697 (2005).
Stallwood et al., "Small Interfering RNA-Mediated Knockdown of Notch Ligands in Primary $CD4^+T$ Cells and Dendritic Cells Enhances Cytokine Production," J. Immunol., 177:885-895 (2006).
Supplementary European Search Report issued in EP09828380 dated Nov. 30, 2012 (8 pages).
Wagers et al., "Little Evidence for Developmental Plasticity of Adult Hematopoietic Stem Cells," Science, 297:2256-2259 (2002).
Wang et al., "Cell fusion is the principal source of bone-marrow-derived hepatocytes," Nature, 422:897-901 (2003).
Warner et al., "Expression of ZIC Genes in the Development of the Chick Inner Ear and Nervous System," Dev. Dyn., 226:702-712 (2003).
Weimann et al., "Contribution of transplanted bone marrow cells to Purkinje neurons in human adult brains," Proc. Natl. Acad. Sci. U.S.A., 100:2088-2093 (2003).
White et al., "Mammalian cochlear supporting cells can divide and trans-differentiate into hair cells," Nature, 441:984-987 (2006).
Woods et al., "Math1 regulates development of the sensory epithelium in the mammalian cochlea," Nat. Neurosci., 7:1310-1318 (2004).
Written Opinion of the International Searching Authority for PCT/US2009/065747, dated Apr. 8, 2010.
Written Opinion of the International Searching Authority issued in corresponding International Application No. PCT/US2007/84654, dated Oct. 3, 2008.
Yamamoto et al., "Inhibition of Notch/RBP-J signaling induces hair cell formation in neonate mouse cochleas," Mol. Med., 84:37-45 (2006).
Zheng et al., "Induction of Cell Proliferation by Fibroblast and Insulin-Like Growth Factors in Pure Rat Inner Ear Epithelial Cell Cultures," J. Neurosci., 17:216-226 (1997).

(56) References Cited

OTHER PUBLICATIONS

Zheng et al., "Overexpression of Math1 induces robust production of extra hair cells in postnatal rat inner ears," Neuroscience, 3(6):580-586 (2000).
Zine et al., "Notch signaling regulates the pattern of auditory hair cell differentiation in mammals," Development, 127:3373-3383 (2000).
Office Action issued in AU2009316264 dated Jan. 16, 2015 (5 pages).
Office Action issued in JP2011-537715 dated Jan. 20, 2015 with English translation (7 pages).
Response to Non-Final Office Action issued in U.S. Appl. No. 13/130,607 dated Oct. 23, 2014, filed Apr. 23, 2015 (10 pages).
U.S. Final Office Action in U.S. Appl. No. 13/130,607, dated Jan. 15, 2016 (26 pages).
Adam et al., "Cell fate choices and the expression of Notch, Delta and Serrate homologues in the chick inner ear: parallels with *Drosophila* sense-organ development," Development, 125(23):4645-54 (Dec. 1998).
Basi et al., "Amyloid precursor protein selective gamma-secretase inhibitors for treatment Amyloid precursor protein selective gamma-secretase of Alzheimer's disease," Alzheimer's Research & Therapy, 2:36 (2010) pp. 1-21.
Batts et al., "Notch signaling and Hes labeling in the normal and drug-damaged organ of Corti," Hear Res., 249:15-22 (Mar. 2009).
Bramhall, "Lgr5-Positive Supporting Cells Generate New Hair Cells in the Postnatal Cochlea," Stem Cell Reports, Mar. 2014, 2:1-12.
Caiazzo et al., "Direct generation of functional dopaminergic neurons from mouse and human fibroblasts," Nature, 476:224-7 (Jul. 2011).
Corwin et al., "Regeneration of Sensory Hair Cells After Acoustic Trauma," Science, Jun. 1988, 240:1772-1774.
Daudet and Lewis, "Two contrasting roles for Notch activity in chick inner ear development: specification of pro sensory patches and lateral inhibition of hair-cell differentiation," Development, 132:541-51 (Feb. 2005).
Daudet et al., "Notch regulation of progenitor cell behavior in quiescent and regenerating auditory epithelium of mature birds," Dev Biol., 326(1):86-100 (Feb. 1, 2009).
Doetzlhofer et al., "Hey2 regulation by FGF provides a Notch-independent mechanism for maintaining pillar cell fate in the organ of Corti," Dev Cell, 16:58-69 (Jan. 2009).
Dong et al., "Calpain inhibitor MDL28170 modulates Aβ formation by inhibiting the formation of intermediate $A\beta_{46}$ and protecting Aβ from degradation," The FASEB Journal, Dec. 2005, 21 pages.
Eatock and Rusch, "Developmental changes in the physiology of hair cells," Cell & Developmental Biology, 1997, 8:265-275.
European Search Report in Application No. 13836099, dated Mar. 8, 2016, 9 Pages.
Goycoolea and Lundman, "Round window membrane. Structure function and permeability: a review," Microsc Res Tech., 36:201-11 (Feb. 1, 1997).
Hadland et al., "γ-secretase inhibitors repress thymocyte development," Proc Natl. Acad Sci USA, 98:7487-91 (Jun. 19, 2001).
Hartman et al., "Hes5 expression in the postnatal and adult mouse inner ear and the drug-damaged cochlea," J. Assoc Res Otolaryngol., 10:321-40 (Sep. 2009).
Hosoya et al., "An efficient screening method using inner-ear derived spheres for selection of compounds that induce hair cell differentiation," Neurosci Res., 61S:S57 Abstract, 2 pages (2008).
Hume et al., "Expression of LHX3 and SOX2 during mouse inner ear development," Gene Expression Patterns, 2007, 7:798-807.
Huynh et al., "The novel gamma secretase inhibitor RO4929097 reduces the tumor initiating potential of melanoma," PLoS One, 6(9):e25264, (2011) 10 pages.
Hyde et al., "Studies to investigate the in vivo therapeutic window of the γ-secretase inhibitor $N^2$-[(2S)-2-(3,5-difluorophenyl)-2-hydroxyethanoyl]-$N^1$-[(7S)-5-methyl-6-oxo-6,7-dihydro-5H-dibenzo[b,d]azepin-7-yl]-$_L$-alaninamide (LY411,575) in the CRND8 mouse," J Pharmacol Exp Ther., 319:1133-43 (Dec. 2006).
International Preliminary Report on Patentability in International Application No. PCT/US2013/058446, dated Mar. 10, 2015, 11 pages.
International Search Report and Written Opinion in International Application No. PCT/US2013/058446, dated Dec. 26, 2013, 8 pages.
Kaneko et al., "Musashi1: an evolutionarily conserved marker for CNS progenitor cells including neural stem cells," Dev Neurosci., 22:139-53 (2000).
Kelley, "Regulation of cell fate in the sensory epithelia of the inner ear," Nat Rev Neurosci., 7:837-49 (Nov. 2006).
Lin et al., "Inhibition of notch activity promotes non-mitotic regeneration of hair cells in the adult mouse utricles," J Neurosci., 31(43):15329-15339 (Oct. 26, 2011).
Luistro et al., "Preclinical Profile of a Potent γ-Secretase Inhibitor Targeting Notch Signaling with In vivo Efficacy and Pharmacodynamic Properties," Cancer Res, Oct. 2009, 69(19):7672-7690.
Lumpkin et al., "Math1-driven GFP expression in the developing nervous system of transgenic mice," Gene Expr Patterns, 3:389-95 (Aug. 2003).
Masuda et al., "Dual antitumor mechanisms of notch signaling inhibitor in a T-cell acute lymphoblastic leukemia xenograft model," Cancer Sci., 100(12):2444-2450 (Dec. 2009).
Mikulec et al., "Permeability of the round window membrane is influenced by the composition of applied drug solutions and by common surgical procedures," Otol Neurotol., 29:1020-6 (Oct. 2008).
Mitani et al., "Differential Effects between γ-Secretase Inhibitors and Modulators on Cognitive Function in Amyloid Precursor Protein-Transgenic and Nontransgenic Mice," J. Neuroscience, Feb. 2012.
Mizutari et al., "Notch Inhibition induces cochlear hair cell regeneration and recovery of hearing after acoustic trauma," Neuron, Jan. 2013, 77(1): 58-69.
Oesterle et al., "Sox2 and JAGGED1 expression in normal and drug-damaged adult mouse inner ear," J Assoc Res Otolaryngol., 9:65-89 (Mar. 2008).
Response to U.S. Final Office Action in U.S. Appl. No. 13/130,607, dated Jan. 15, 2016.
Rubel et al., "Mammalian Vestibular Hair Cell Regeneration," Science, Feb. 1995, 267(5198):701-707.
Ryals and Rubel, "Hair Cell Regeneration After Acoustic Trauma in Adult Coturnix Quail," Science, Jun. 1988, 240:1774-1776.
Ryusuke et al., "Pharmacological inhibition of Notch signaling in the mature guinea pig cochlea" Neuroreport, Lippincott Williams and Wilkins, UK, Dec. 2007, 18(18): 1911-1914.
Sakaguchi et al., "Spatiotemporal patterns of Musashi1 expression during inner ear development," Neuroreport, 15:997-1001 (Apr. 29, 2004).
Salt and Plontke, "Principles of local drug delivery to the inner ear," Audiol Neurootol., 14:350-60 (2009).
Samon et al., "Preclinical analysis of the γ-secretase inhibitor PF-03084014 in combination with glucocorticoids in T-cell acute lymphoblastic leukemia," Mol Cancer Ther., 11(7):1565-1575 (Jul. 2012).
Vierbuchen et al., "Direct conversion of fibroblasts to functional neurons by defined factors," Nature, 463:1035-41 (Feb. 25, 2010).
Wang et al., "Dynamics of noise-induced cellular injury and repair in the mouse cochlea," J Assoc Res Otolaryngol., 3:248-68 (Sep. 2002).
Wolfe, "γ-secretase Inhibition and Modulation for Alzheimer's Disease," Curr Alzheimer Res., 5(2):158-164 (Apr. 2008) (Author Manuscript).
Wong et al., "Chronic treatment with the gamma-secretase inhibitor LY-411,575 inhibits beta-amyloid peptide production and alters lymphopoiesis and intestinal cell differentiation," J Biol Chem., 279:12876-82 (Mar. 26, 2004).
Zine et al., "Hes1 and Hes5 activities are required for the normal development of the hair cells in the mammalian inner ear," J Neurosci., 21:4712-20 (Jul. 1, 2001).

(56) References Cited

OTHER PUBLICATIONS

Office Action issued in JP2015-178811 dated Mar. 7, 2017 with English translation (5 pages).

* cited by examiner

Fig. 1D
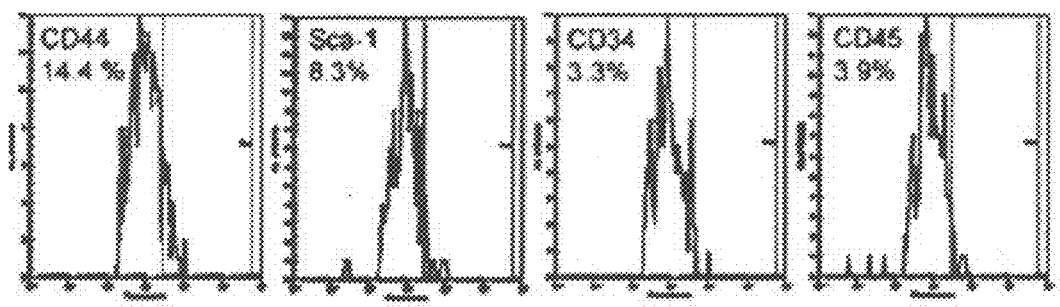
Fig. 1E
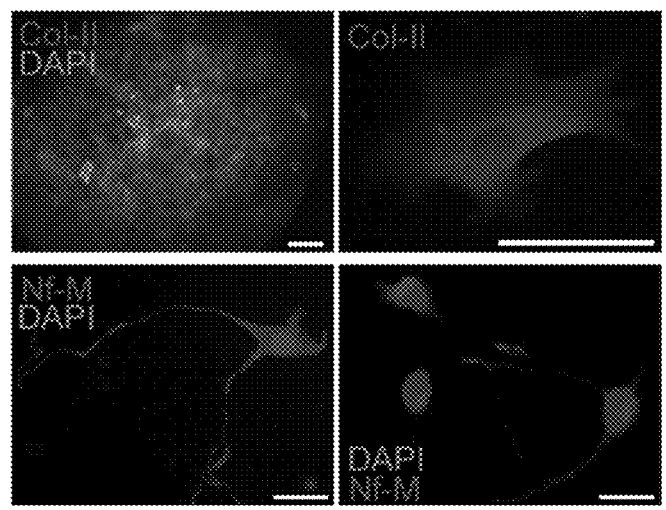
Fig. 1F

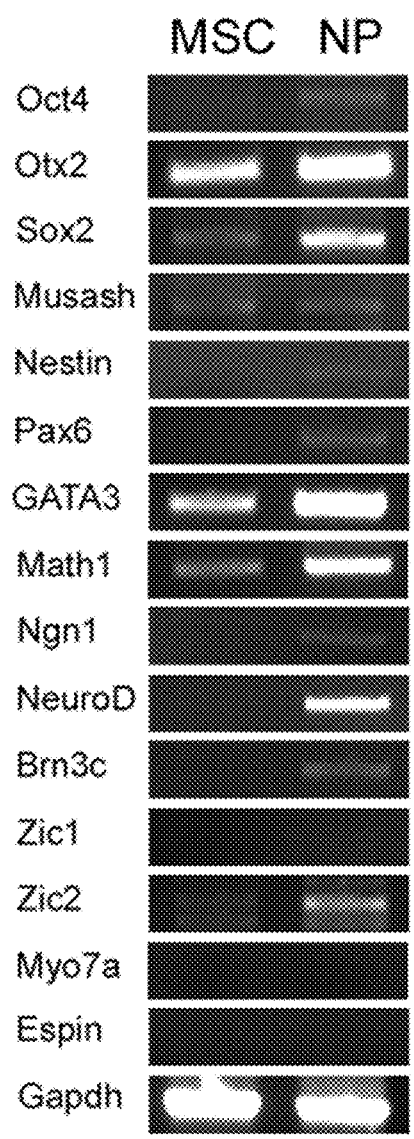
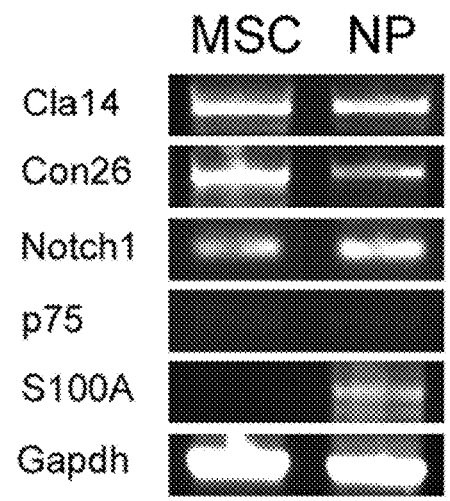
Fig. 3A
Fig. 3B

Math-1 transfection

Math-1 transfection

GENERATION OF INNER EAR AUDITORY HAIR CELL

CLAIM OF PRIORITY

This application is continuation application of U.S. patent application Ser. No. 13/759,441, filed Feb. 5, 2013, which is a continuation application of U.S. patent application Ser. No. 12/233,017, filed Sep. 18, 2008, which is a continuation of International Patent Application No. PCT/US2007/084654, filed on Nov. 14, 2007, which claims the benefit of U.S. Provisional Patent Application Ser. No. 60/859,041, filed on Nov. 15, 2006; the entire contents of each of the foregoing applications are hereby incorporated by reference.

FEDERALLY SPONSORED RESEARCH OR DEVELOPMENT

This invention was made with Government support under Grant No. F33 DC006789, RO1 DC007174, and P30 DC05209 from the National Institute on Deafness and other Communicative Disorders (NIDCD) of the National Institutes of Health. The Government has certain rights in the invention.

TECHNICAL FIELD

This invention relates to methods using bone marrow mesenchymal stem cells to regenerate inner ear cells, e.g., hair cells and supporting cells, to treat inner ear damage.

BACKGROUND

A source of sensory cells and neurons for regeneration of inner ear cells would provide a valuable tool for clinical application because neurons and hair cells could be employed in cell replacement therapy for hearing loss. Recent work has shown that hair cells and neurons can be differentiated from endogenous stem cells of the inner ear (Li et al., Nat Med 9, 1293-1299 (2003); Rask-Andersen et al., Hear Res 203, 180-191 (2005)) and other work has shown that endogenous cells of the sensory epithelium can be converted to hair cells when the proneural transcription factor, Atoh1, is expressed exogenously (Izumikawa et al., Nat Med 11, 271-276 (2005); Zheng and Gao, Nat Neurosci 3, 580-586 (2000)) and yet the endogenous stem cells of the inner ear do not spontaneously generate hair cells. Injection of whole bone marrow to reconstitute a lethally irradiated mouse resulted in engraftment of these cells in areas occupied by inner ear mesenchymal cells and fibrocytes but did not yield hair cells (Lang et al., J Comp Neurol 496, 187-201 (2006)).

SUMMARY

The present invention is based, at least in part, on the discovery of methods that can be used to induce stem cells to differentiate into hair cells and supporting cells. Thus, described herein are methods for providing populations of hair cells and/or supporting cells, compositions comprising said cells, and methods of use thereof, e.g., for the treatment of subjects who have or are at risk of developing a hearing loss.

In one aspect, the invention provides methods for providing populations of hair cells and/or supporting cells. The methods include:

obtaining a population of stem cells with neurogenic potential;

culturing the stem cells under conditions sufficient to induce the differentiation of at least some of the stem cells into inner ear progenitor cells, and doing one (or more) of the following:

(i) inducing the expression of Atoh1 in the inner ear progenitor cells, in an amount and for a time sufficient to induce at least some of the inner ear progenitor cells to differentiate into hair cells;

(ii) contacting the inner ear progenitor cells with an inhibitor of Notch signalling (e.g., a gamma-secretase inhibitor or inhibitory nucleic acid), in an amount and for a time sufficient to induce at least some of the inner ear progenitor cells to differentiate into hair cells; or (iii) culturing the inner ear progenitor cells in the presence of chick otocyst cells for a time and under conditions sufficient for at least some of the inner ear progenitor cells to differentiate into hair cells, thereby providing populations of hair cells and/or supporting cells.

In some embodiments, the methods include isolating the inner ear progenitor cells, hair cells, and/or supporting cells, e.g., to provide a purified population thereof.

In some embodiments, the inner ear progenitor cells express nestin, sox2, musashi, Brn3C, Pax2, and Atoh1.

In some embodiments, the hair cells express one or more genes selected from the group consisting of Atoh1, jagged 2, Brn3c, p27Kip, Ngn1, NeuroD, myosin VIIa and espin. In some embodiments, the hair cells express jagged 2, Brn3c, myosin VIIa and espin. In some embodiments, the hair cells express F-actin in a V pattern on the apical surface of the cells.

In some embodiments, the supporting cells express one or more of claudin14, connexin 26, $p75^{Trk}$, Notch 1, and S100A.

In some embodiments, the methods further include transplanting the hair cells or supporting cells into a subject in need thereof, e.g., into or near the sensory epithelium of the subject. In some embodiments, the population of stem cells is obtained from a subject in need of the transplant.

Also described herein are isolated populations of hair cells, supporting cells, and inner ear progenitor cells obtained by a method described herein.

In another aspect, the invention features methods for treating a subject who has or is at risk for developing a disorder, e.g., a hearing disorder or vestibular disorder, wherein the disorder is treatable with a transplant of hair cells and/or supporting cells, the method comprising transplanting cells obtained by a method described herein into the cochlea of the subject, thereby treating the subject. In these embodiments, it is preferable if the population of stem cells was obtained from the subject in need of the transplant.

In some embodiments, inducing the expression of Atoh1 in the cells comprises inducing the expression of exogenous Atoh1 in the cells, e.g., by transducing the cells with a vector encoding a Atoh1 polypeptide, e.g., a plasmid vector or a viral vector, e.g., an adenovirus, lentivirus, or retrovirus.

In some embodiments, inducing the expression of exogenous Atoh1 in the stem cells comprises increasing expression of endogenous Atoh1, e.g., by increasing activity of the Atoh1 promoter or by replacing the endogenous Atoh1 promoter with a more highly active promoter.

In some embodiments, culturing the stem cells in the presence of chick otocyst cells for a time and under conditions sufficient for at least some of the stem cells to differentiate into hair cells comprises culturing the stem cells in medium comprising IGF, EGF, and FGF.

In some embodiments, the stem cells used in the methods described herein are mesenchymal stem cells. In some embodiments, the stem cells used in the methods described herein are human stem cells.

As noted, the invention also features cells isolated by a method described herein, as well as compositions containing them.

Methods for treating subjects (e.g., mammals such as humans) who have, or who are at risk for developing, a hearing loss, are also described herein. These methods include administering a cell or population of cells (as described herein; e.g., a population of hair cells obtained by differentiating a population of stem cells) to the ear of the patient, e.g., to the cochlea. The administered cells may be obtained by the methods described herein, and the starting material may be stem cells obtained from the patient to be treated.

There may be certain advantages to the use of the cells described herein for the treatment of hearing loss. For example, the stem cells can be obtained from humans for clinical applications. Because the stem cells can be harvested from a human, and in particular can be harvested from the human in need of treatment, the immunological hurdles common in xeno- and allotransplantation experiments can be largely avoided.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1D is a row of four plots showing the results of analysis of bone marrow MSCs by chip flow cytometry indicating the ratio of immunopositive cells for each of the listed antibodies (CD44, first panel; Sca-1, second panel; CD34, third panel; and CD45, last panel); axes are "Fluorescence" and "No. of events."

FIG. 1E is a pair of photomicrographs showing the potential for lineage differentiation, as demonstrated by formation of chondrocytes and extracellular matrix after treatment of bone marrow MSCs with TGF-β. Cells that grew out from a micro-aggregate (left) were stained for type II collagen (right).

FIG. 1F is a pair of photomicrographs showing the differentiation of bone marrow MSCs to neurons by differentiation in serum-free medium containing neuronal growth supplements and bFGF. Staining for neurofilament (NF-M) is shown in these cells.

FIG. 3A is a gel showing the results of genetic analysis by RT-PCR of precursor cells incubated in NT3, FGF and BDNF (which support neuronal and sensory cell progenitors in the inner ear). The gene profiles included expression of Oct4, nestin, Otx2, and Musashi, as well as proneural transcription factors, GATA3, NeuroD, Ngn1, Atoh1, Brn3c, and Zic2. These cells did not express hair cells genes, myosin VIIa and espin.

FIG. 3B is a gel showing the results of genetic analysis by RT-PCR of the cells obtained after induction with NT3, FGF, and BDNF. Genes characteristic of supporting cells (claudin14, connexin 26, $p75^{Trk}$, Notch 1, and S100A) were also observed. These progenitor cells thus had expression profiles characteristic of neuronal or sensory progenitors. Genes analyzed are shown to the left of the gels.

DETAILED DESCRIPTION

Figure 1A:
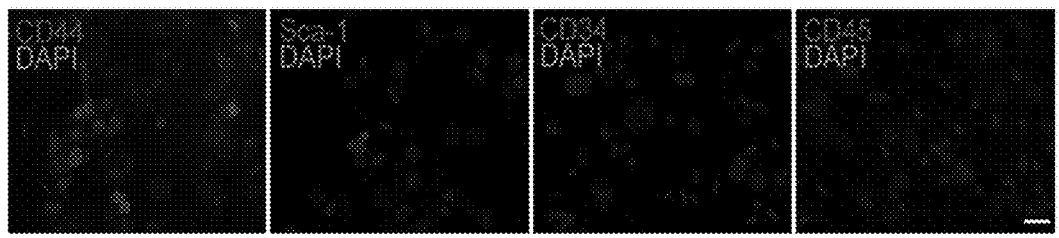
FIG. 1A is a row of four photomicrographs of bone marrow MSCs from passage 3 immunostained with antibodies against CD44, CD45, CD34 and Sca-1 followed by secondary antibodies against mouse immunoglobulins labeled with TRITC (medium gray, shown in red in the original). Staining for CD34 and CD45 was negative, but CD44 and Sca-1 were expressed. Nuclei were stained with DAPI (darker gray, blue in the original).

Although stem cells are present in the inner ear (Li et al., Trends Mol Med 10, 309-315 (2004); Li et al., Nat Med 9, 1293-1299 (2003); Rask-Andersen et al., Hear Res 203, 180-191 (2005)), hair cells do not regenerate after damage, and, therefore, a source of cells that could potentially be used for cell transplantation in a therapeutic replacement of these sensory cells has important implications for treatment of sensorineural hearing loss. Bone marrow has been harvested and used extensively in clinical applications and is a highly desirable source, because cells from a patient's bone marrow could potentially be transplanted without the problem of immune rejection. The present methods include a treatment regimen for hearing loss including transplantation of hair cells obtained by methods described herein.

By a combination of growth factor stimulation and expression of the transcription factor, Atoh1, that is required for hair cell formation in the inner ear, the present inventors demonstrate herein that stem cells, e.g., mesenchymal stem cells derived from bone marrow, can be induced to differentiate into hair cells. In addition, the neurosensory progenitors obtained from bone marrow can be converted to sensory cells by co-culture with cells of the developing sensory epithelium, even in the absence of Atoh1 expression.

Stem cells in bone marrow are known to be the precursors for all lymphoid and erythroid cells, but mesenchymal stem cells in bone marrow also act as precursors to bone, cartilage, and fat cells (Colter et al., Proc Natl Acad Sci USA 97, 3213-3218 (2000); Pittenger et al., Science 284, 143-147 (1999)). In addition to mesenchymal tissues, these stem cells have been shown to give rise to cells of other lineages including pancreatic cells (Hess et al., Nat Biotechnol 21, 763-770 (2003)), muscle cells (Doyonnas et al., Proc Natl Acad Sci USA 101, 13507-13512 (2004)) and neurons (Dezawa et al., J Clin Invest 113, 1701-1710 (2004); Hermann et al., J Cell Sci 117, 4411-4422 (2004); Jiang et al., Proc Natl Acad Sci USA 100 Suppl 1, 11854-11860 (2003)). The evidence provided herein demonstrates an extended range of cell fates available for these bone marrow-derived cells that includes cells of the neurosensory lineage, even including differentiation to inner ear hair cells.

Methods for Generating Cells of the Inner Ear

Methods of generating cells of the inner ear are provided, including progenitor cells and differentiated inner ear cells including hair cells and supporting cells. Stem cells are unspecialized cells capable of extensive proliferation. Stem cells are pluripotent and are believed to have the capacity to differentiate into most cell types in the body (Pedersen, Scientif. Am. 280:68 (1999)), including neural cells, muscle cells, blood cells, epithelial cells, skin cells, and cells of the inner ear (e.g., hair cells and cells of the spiral ganglion). Stem cells are capable of ongoing proliferation in vitro without differentiating. As they divide, they retain a normal karyotype, and they retain the capacity to differentiate to produce adult cell types.

Hematopoietic stem cells resident in bone marrow are the source of blood cells, but in addition to these hematopoietic stem cells, the bone marrow contains mesenchymal stem cells (MSCs) that can differentiate into cell types of all three embryonic germ layers (Colter et al., Proc Natl Acad Sci USA 97, 3213-3218 (2000); Doyonnas et al., Proc Natl Acad Sci USA 101, 13507-13512 (2004); Herzog et al., Blood 102, 3483-3493 (2003); Hess et al., Nat Biotechnol 21, 763-770 (2003); Jiang et al., Nature 418, 41-49 (2002); Pittenger et al., Science 284, 143-147 (1999)). This has been demonstrated in vivo in studies that track transplanted bone marrow cells to specific tissues where they differentiate into the resident tissue type (Mezey et al., Proc Natl Acad Sci USA 100, 1364-1369 (2003); Weimann et al., Proc Natl Acad Sci USA 100, 2088-2093 (2003)).

Many of these cells have been used for transplantation and are a preferred source of new cells for therapies because the transplanted cells are immunologically matched when harvested from a patient to be treated and because they have been extensively used in clinical applications so that their safety is known.

Stem cells can differentiate to varying degrees. For example, stem cells can form cell aggregates called embryoid bodies in hanging drop cultures. The embryoid bodies contain neural progenitor cells that can be selected by their expression of an early marker gene such as Sox1 and the nestin gene, which encodes an intermediate filament protein (Lee et al., Nat. Biotech. 18:675-9, 2000).

Neurogenic Stem Cells

Inner ear cells or inner ear cell progenitors can be generated from mammalian stem cells. As described herein, stem cells suitable for use in the present methods can be any stem cell that has neurogenic potential, i.e., any stem cell that has the potential to differentiate into a neural cell, e.g., neurons, glia, astrocytes, retinal photoreceptors, oligodendrocytes, olfactory cells, hair cells, supporting cells, and the like. Neurogenic stem cells, including human adult stem cells such as bone marrow mesenchymal stem cells, can be induced to differentiate into inner ear progenitor cells that are capable of giving rise to mature inner ear cells including hair cells and supporting cells. Neurogenic stem cells useful in the methods described herein can be identified by the expression of certain neurogenic stem cell markers, such as nestin, sox1, sox2, and musashi. Alternatively or in addition, these cells express high levels of helix-loop-helix transcription factors NeuroD, Atoh1, and neurogenin1.

Examples of neurogenic stem cells include embryonic stem cells or stem cells derived from mature (e.g., adult) tissue, such as the ear (e.g., inner ear), central nervous system, blood, skin, eye or bone marrow. In some embodiments, the stem cells are mesenchymal stem cells. Any of the methods described herein for culturing stem cells and inducing differentiation into inner ear cells (e.g., hair cells or supporting cells) can be used.

Stem cells useful for generating cells of the inner ear can be derived from a mammal, such as a human, mouse, rat, pig, sheep, goat, or non-human primate. For example, stem cells have been identified and isolated from the mouse utricular macula (Li et al., Nature Medicine 9:1293-1299, 2003).

Generation of Neural Progenitor Cells

There are a number of induction protocols known in the art for inducing differentiation of stem cells with neurogenic potential into neural progenitor cells, including growth factor treatment (e.g., treatment with EGF, FGF, and IGF, as described herein) and neurotrophin treatment (e.g., treatment with NT3 and BDNF, as described herein). Other differentiation protocols are known in the art; see, e.g., Corrales et al., J. Neurobiol. 66(13):1489-500 (2006); Kim et al., Nature 418, 50-6 (2002); Lee et al., Nat Biotechnol 18, 675-9 (2000); and Li et al., Nat Biotechnol 23, 215-21 (2005).

As one example of an induction protocol, the stem cells are grown in the presence of supplemental growth factors that induce differentiation into progenitor cells. These supplemental growth factors are added to the culture medium. The type and concentration of the supplemental growth factors is be adjusted to modulate the growth characteristics of the cells (e.g., to stimulate or sensitize the cells to differentiate) and to permit the survival of the differentiated cells such as neurons, glial cells, supporting cells or hair cells.

Exemplary supplementary ng/mL, about 50 ng/mL, about 40 ng/mL, about 30 ng/mL, about 20 ng/mL, about 10 ng/mL, or about 5 ng/mL).

Neural progenitor cells produced by these methods include inner ear progenitor cells, i.e., cells that can give rise to inner ear cells such as hair cells and supporting cells. Inner ear progenitor cells can be identified by the expression of marker genes such as nestin, sox2, and musashi, in addition to certain inner-ear specific marker genes Brn3C, Pax2, and Atoh1. The invention includes purified populations of inner ear progenitor cells expressing nestin, sox2, musashi, Brn3C, Pax2, and Atoh1. These inner ear progenitor cells are lineage committed, and can be induced to further differentiate into hair cells and supporting cells by a method described herein.

Progenitor cells prepared by a method described herein can optionally be frozen for future use.

Cell Culture Methods

In general, standard culture methods are used in the methods described herein. Appropriate culture medium is described in the art, such as in Li et al. (supra). For example, stem cells can be cultured in serum free DMEM/high-glucose and F12 media (mixed 1:1), and supplemented with N2 and B27 solutions and growth factors. Growth factors such as EGF, IGF-1, and bFGF have been demonstrated to augment sphere formation in culture. In vitro, stem cells often show a distinct potential for forming spheres by proliferation of single cells. Thus, the identification and isolation of spheres can aid in the process of isolating stem cells from mature tissue for use in making differentiated cells of the inner ear. The growth medium for cultured stem cells can contain one or more or any combination of growth factors. This includes leukemia inhibitory factor (LIF) which prevents the stem cells from differentiating. To induce the cells (and the cells of the spheres) to differentiate, the medium can be exchanged for medium lacking growth factors. For example, the medium can be serum-free DMEM/high glucose and F12 media (mixed 1:1) supplemented with N2 and B27 solutions. Equivalent alternative media and nutrients can also be used. Culture conditions can be optimized using methods known in the art.

growth factors are discussed in detail below, and include, but are not limited to basic fibroblast growth factor (bFGF), insulin-like growth factor (IGF), and epidermal growth factor (EGF). Alternatively, the supplemental growth factors can include the neurotrophic factors neurotrophin-3 (NT3) and brain derived neurotrophic factor (BDNF). Concentrations of growth factors can range from about 100 ng/mL to about 0.5 ng/mL (e.g., from about 80 ng/mL to about 3 ng/mL, such as about 60

Differentiation by Expression of Atoh1

As described herein, expression of Atoh1 in stem-cell derived progenitor cells was sufficient to drive them into adopting hair cell markers. Studies of Atoh1 expression in the ear have indicated that this helix-loop-helix transcription factor occupies a key place in the hierarchy of inner ear transcription factors for differentiation of hair cells.

Atoh1 nucleic acids and polypeptides are known in the art, and described in, for example, U.S. Pat. Nos. 6,838,444 and 7,053,200, and P.G. PUB. Nos. 2004/0237127 and 2004/0231009, all to Zoghbi et al., all incorporated by reference in their entirety. In some embodiments, the Atoh1 is, or is at least 80%, 85%, 90%, 93%, or 95% identical to, human atonal homolog 1 (ATOH1); ATH1; and HATH1 (for additional information see Ben-Arie et al., Molec. Genet. 5: 1207-1216 (1996); Bermingham et al., Science 284: 1837-1841 (1999); OMIM*601461; UniGene Hs.532680; Gen-Bank Accession Nos. NM_005172.1 (nucleic acid) and NP_005163.1 (polypeptide)). Other species can also be used, e.g., Mouse Atoh1 (also known as Math1, GenBank Acc. No. NM_007500.2), chicken Atoh1 (also known as Cath1; GenBank Acc. No. AF467292.1).

The human Atoh1 mRNA (CDS=−1065) and polypeptide sequences are as follows:

```
                                                           (SEQ ID NO: 1)
   1  atgtcccgcc tgctgcatgc agaagagtgg gctgaagtga aggagttggg agaccaccat
  61  cgccagcccc agccgcatca tctcccgcaa ccgccgccgc cgccgcagcc acctgcaact
 121  ttgcaggcga gagagcatcc cgtctacccg cctgagctgt ccctcctgga cagcaccgac
 181  ccacgcgcct ggctggctcc cactttgcag ggcatctgca cggcacgcgc cgcccagtat
 241  ttgctacatt ccccggagct gggtgcctca gaggccgctg cgcccggga cgaggtggac
 301  ggccggggg agctggtaag gaggagcagc ggcggtgcca gcagcagcaa gagccccggg
 361  ccggtgaaag tgcgggaaca gctgtgcaag ctgaaaggcg gggtggtggt agacgagctg
 421  ggctgcagcc gccaacgggc ccttccagc aaacaggtga atgggtgca gaagcagaga
 481  cggctagcag ccaacgccag ggagcggcgc aggatgcatg ggctgaacca cgccttcgac
 541  cagctgcgca atgttatccc gtcgttcaac aacgacaaga gctgtccaa atatgagacc
 601  ctgcagatgg cccaaatcta catcaacgcc ttgtccgagc tgctacaaac gcccagcgga
 661  ggggaacagc caccgccgcc tccagcctcc tgcaaaagcg accaccacca ccttcgcacc
 721  gcggcctcct atgaagggg cgcgggcaac gcgaccgcag ctgggctca gcaggcttcc
 781  ggagggagcc agcggccgac cccgcccggg agttgccgga ctcgcttctc agccccagct
 841  tctgcgggag ggtactcggt gcagctggac gctctgcact tctcgacttt cgaggacagc
 901  gccctgacag cgatgatggc gcaaaagaat ttgtctcctt ctctccccgg gagcatcttg
 961  cagccagtgc aggaggaaaa cagcaaaact tcgcctcggt cccacagaag cgacggggaa
1021  ttttcccccc attcccatta cagtgactcg gatgaggcaa gttag
```

```
                                                                  (SEQ ID NO: 2)
MSRLLHAEEWAEVKELGDHHRQPQPHHLPQPPPPPQPPATLQAREHPVYP

PELSLLDSTDPRAWLAPTLQGICTARAAQYLLHSPELGASEAAAPRDEVD

GRGELVRRSSGGASSSKSPGPVKVREQLCKLKGGVVVDELGCSRQRAPSS

KQVNGVQKQRRLAANARERRRMHGLNHAFDQLRNVIPSFNNDKKLSKYET

LQMAQIYINALSELLQTPSGGEQPPPPPASCKSDHHHLRTAASYEGGAGN

ATAAGAQQASGGSQRPTPPGSCRTRFSAPASAGGYSVQLDALHFSTFEDS

ALTAMMAQKNLSPSLPGSILQPVQEENSKTSPRSHRSDGEFSPHSHYSDS

DEAS
```

The mouse Atoh1 mRNA (CDS=196-1251) and polypeptide sequences are as follows:

```
                                                           (SEQ ID NO: 3)
   1  tcgacccacg cgtccgccca cgcgtccgga tctccgagtg agaggggag ggtcagagga
  61  ggaaggaaaa aaaaatcaga ccttgcagaa gagactagga aggttttgt tgttgttgtt
 121  cggggcttat ccccttcgtt gaactgggtt gccagcacct cctctaacac ggcacctccg
 181  agccattgca gtgcgatgtc ccgcctgctg catgcagaag agtgggctga ggtaaaagag
```

-continued

```
 241  ttgggggacc accatcgcca tccccagccg caccacgtcc cgccgctgac gccacagcca
 301  cctgctaccc tgcaggcgag agaccttccc gtctacccgg cagaactgtc cctcctggat
 361  agcaccgacc cacgcgcctg gctgactccc actttgcagg gcctctgcac ggcacgcgcc
 421  gcccagtatc tgctgcattc tcccgagctg ggtgcctccg aggccgcggc gccccgggac
 481  gaggctgaca gccagggtga gctggtaagg agaagcggct gtggcggcct cagcaagagc
 541  cccgggcccg tcaaagtacg ggaacagctg tgcaagctga agggtggggt tgtagtggac
 601  gagcttggct gcagccgcca gcgagcccct tccagcaaac aggtgaatgg ggtacagaag
 661  caaaggaggc tggcagcaaa cgcaagggaa cggcgcagga tgcacgggct gaaccacgcc
 721  ttcgaccagc tgcgcaacgt tatcccgtcc ttcaacaacg acaagaagct gtccaaatat
 781  gagaccctac agatggccca gatctacatc aacgctctgt cggagttgct gcagactccc
 841  aatgtcggag agcaaccgcc gccgcccaca gcttcctgca aaaatgacca ccatcacctt
 901  cgcaccgcct cctcctatga aggaggtgcg ggcgcctctg cggtagctgg ggctcagcca
 961  gccccgggag ggggcccgag acctacccccg cccgggcctt gccggactcg cttctcaggc
1021  ccagcttcct ctgggggtta ctcggtgcag ctggacgctt tgcacttccc agccttcgag
1081  gacagggccc taacagcgat gatggcacag aaggacctgt cgccttcgct gccgggggc
1141  atcctgcagc ctgtacagga ggacaacagc aaaacatctc ccagatccca cagaagtgac
1201  ggagagtttt ccccccactc tcattacagt gactctgatg aggccagtta ggaaggcaac
1261  agctccctga aaactgagac aaccaaatgc ccttcctagc gcgcgggaag ccccgtgaca
1321  aatatccctg caccctttaa ttttttggtct gtggtgatcg ttgttagcaa cgacttgact
1381  tcggacggct gcagctcttc caatccccct cctcctacct tctccttcct ctgtatgtag
1441  atactgtatc attatatgta cctttacgtg gcatcgtttc atggtccatg ctgccaatat
1501  gctgctaaaa tgtcgtatct ctgcctctgg tctgggtttc acttattta taccttggga
1561  gttcatcctt gcgtgttgcg ctcactcaca ataaggagg ttagtcaatg aagttgtttc
1621  cccaactgct tgagaccccgc attgggtact ttactgaaca cggactattg tgttgttaaa
1681  atgcaggggc agataagagt atctgtagag cttagacacc aagtgtgtcc agcagtgtgt
1741  ctagcggacc cagaatacac gcacttcatc actggccgct gcgccgcctt gaagaaactc
1801  aactgccaat gcagagcaac ttttgatttt aaaaacagcc actcataatc attaaactct
1861  ttgcaaatgt tgttttttgc aaatgaaaat taaaaaaaaa catgtagtgt caaaggcatt
1921  tggtcaattt tattttgctt tgttaacatt agaaaagtta tttattattg cgtatttgga
1981  cccatttcta cttaattgcc ttttttttac attttctact cgagatcgtt ttattttgat
2041  ttagcaaatc cagttgccat tgctttatgt atgtatgctc ttttacaaat gataaaataa
2101  actcggaaaa aaaaaaaaaa aaaaaaaaaa aaaaaaaaaa aaaa
```

(SEQ ID NO: 4)

MSRLLHAEEWAEVKELGDHHRHPQPHHVPPLTPQPPATLQARDLLVRRSG

CGGLSKSPGPVKVREQLCKLKGGVVVDELGCSRQRAPSSKQVNGVQKQRR

LAANARERRRMHGLNHAFDQLRNVIPSFNNDKKLSKYETLQMAQIYINAL

SELLQTPNVGASSGGYSVQLDALHFPAFEDRALTAMMAQKDLSPSLPGGI

LQPVQEDNSKTSPRSHRSDGEFSPHSHYSDSDEAS

The chicken Cath1 mRNA (CDS=1-717) and polypeptide sequences are as follows:

(SEQ ID NO: 5)

```
  1 atggcccag gaggtagcga gtgttgttgc agtgatgccg cgcacatcac ttggaggcag 61 tgggagtaca cgcacgagaa ccaactgtgc gtggcaggaa ctgtcagcag gatgaggccc 121 aggacgtggg tctgcaccgg atctttgtgg gaccaggaag cgggaattac tttgatgggc 181 ccccaaatac ccaaagtgga tgaggcagga gtgatgaccc acccggcaag gtcgctttgc 241 agcactgggg cacatccgtg tcccggggtg gtcgtgctgc ccacgggtgg gatagggcag 301 ccttcaaaga agctctccaa gtacgagacg ctgcagatgg cgcaaatcta catcagcgcc 361 ctcgccgagc ttctgcacgg gccgcccgcg cccccgagc cgcccgccaa ggccgagctc 421 cgcgggccc ccttcgagcc tccccgccg ccccctcctc cgccgcccg cgcctcgccc 481 cccgcgcccg ccaggactcg cttcccccg gcggcggccg cgggcggttt cgcggcgctt 541 ctcgagccgc tgcgcttccc ttctttcccg gcgcagaaag cgccttctcc cgcgctgctc 601 ctggggccgc ccgcgccgca gcagcccgag aggagcaaag cgtcgccgcg ctctcaccgc 661 agcgacgggg agttctcgcc gcgctcccac tacagtgact cggacgaggc cagctag
```

(SEQ ID NO: 6)

MAPGGSECCCSDAAHITWRQWEYTHENQLCVAGTVSRMRPRTWVCTGSLWDQEAGI

TLMGPQIPKVDEAGVMTHPARSLCSTGAHPCPGVVVLPTGGIGQPSKKLSKYETLQ

MAQIYISALAELLHGPPAPPEPPAKAELRGAPFEPPPPPPPPPRASPPAPARTRF

PPAAAAGGFAALLEPLRFPSFPAQKAPSPALLLGPPAPQQPERSKASPRSHRSDGE

FSPRSHYSDSDEAS

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90% or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

For purposes of the present invention, the comparison of sequences and determination of percent identity between two sequences can be accomplished using a Blossum 62 scoring matrix with a gap penalty of 12, a gap extend penalty of 4, and a frameshift gap penalty of 5.

In some embodiments, the methods include expressing in the cells a Atoh1 polypeptide encoded by a nucleic acid that hybridizes to the human Atoh1 mRNA under stringent conditions. As used herein, the term "stringent conditions" describes conditions for hybridization and washing. Stringent conditions as used herein are 0.5M sodium phosphate, 7% SDS at 65° C., followed by one or more washes at 0.2×SSC, 1% SDS at 65° C. See, e.g., *Current Protocols in Molecular Biology*, John Wiley & Sons, N.Y. (2006).

In some embodiments, the methods include expressing exogenous Atoh1 in a stem cell. This can be achieved, for example, by introducing an expression vector in the cell. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a Atoh1 nucleic acid in a form suitable for expression of the nucleic acid in a host cell. Generally, the expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors can be introduced into host cells using methods known in the art, including calcium phosphate or calcium chloride co-precipitation, DEAE-dextran-mediated transfection, lipofection, or electroporation. See, e.g., *Current Protocols in Molecular Biology*, John Wiley & Sons, N.Y. (2006).

In the present methods, the Atoh1 polypeptide expressed in the stem cells will have the ability to induce differentiation of mesenchymal stem cells to hair cells and/or supporting cells, as described herein.

Differentiation by Culturing with Chick Otocysts

Also as described herein, the stem cell-derived progenitor cells also responded to physical contact with developing otocyst cells from the chicken embryo by differentiating into sensory epithelial cells, without the requirement for exogenous Atoh1. This was evidenced by nGFP expression from a Atoh1 enhancer-GFP reporter construct and co-expression of myosin VIIa after co-culture and differentiation, as described herein. Neurons that express markers of sensory cells have been induced from bone marrow MSCs in previous work by incubation with otocyst and hindbrain-conditioned medium (Kondo et al., Proc Natl Acad Sci USA 102, 4789-4794 (2005)) from embryonic mice.

Thus, the methods described herein can include contacting progenitor cells with otocyst cells, e.g., cells isolated from E3 embryonic chicks, as described herein.

In some embodiments, the methods include culturing the progenitor cells with the otocyst cells in a ratio of about 50,000 cells per confluent layer of otocyst cells, or by injection of 100,000 cells into an intact otocyst (see Examples, below). Alternatively, the stem cells can be cultured in the presence of chick otocyst-conditioned media, which can be produced using methods known in the art, e.g., using media that has been in contact with a culture of chick otocysts for at about four days.

Differentiation by Inhibition of Notch Signalling

Notch is a plasma membrane receptor, and the Notch pathway consists of Notch and its ligands, as well as intracellular proteins that transmit the Notch signal to the nucleus. Included in the Notch pathway are the transcription factors that bear the effector function of the pathway.

Notch signaling plays a role in lateral inhibition, in which one cell is singled out from a cell cluster for a given fate (e.g., differentiation into a hair cell, for example). Differentiation is inhibited in those cells not selected to differentiate, resulting in the prevention of a specified fate commitment on the part of most of the cells of a cluster. Lateral inhibition occurs repeatedly during development. Central to this process is binding to the Notch receptor of one of several ligands, including Delta, Scabrous and Serrate. Ligand binding to Notch ligand triggers a chain of intracellular events resulting in lateral inhibition. A review of the Notch pathway can be found at Artavanis-Tsakonas et al., Science 268: 225-232 (1995). As described herein, inhibition of Notch in the inner ear progenitor cells described herein results in differentiation of the cells into hair cells and supporting cells.

Thus, in some embodiments of the methods described herein, progenitor cells are grown in the presence of a Notch signalling pathway inhibitor. Exemplary Notch pathway inhibitors include γ-secretase inhibitors, of which a number are known in the art (e.g., arylsulfonamides (AS), dibenzazepines (DBZ), benzodiazepines (BZ), N—[N-(3,5-difluorophenacetyl)-L-alanyl]-(S)-phenylglycine t-butyl ester (DAPT), L-685,458 (Sigma-Aldrich), and MK0752 (Merck). A useful concentration will depend on the inhibitor chosen.

Other Notch inhibitors include inhibitory nucleic acids (e.g., small interfering RNAs, antisense oligonucleotides, and morpholino oligos; methods for designing, making, and using them are known in the art, e.g., gene walk methods for selecting and optimizing inhibitory sequences, see, e.g., Engelke, *RNA Interference (RNAi): The Nuts & Bolts of siRNA Technology*, (DNA Press, 2004); Mol, *Antisense Nucleic Acids and Proteins*, (CRC, 1994); Sioud, *Ribozymes and Sirna Protocols (Methods in Molecular Biology)*, (Humana Press; 2nd edition 2004); and Philips, *Antisense Therapeutics (Methods in Molecular Medicine)*, (Humana Press 2004)) targeting Notch (see, e.g., Presente et al., Proc. Nat. Acad. Sci. 101(6):1764-1768 (2004); Ivanov et al., Proc. Nat. Acad. Sci. 101(46):16216-16221 (2004)) or its ligands, i.e., Delta or Jagged (see, e.g., Patzel et al., Nature Biotechnology 23, 1440-1444 (2005); Purow et al., Cancer Research 65:2353-2363 (2005); or Stallwood et al., J. Immunol. 177:885-895 (2006)). Alternatively, the cells can be modified to express m-Numb (GenBank Acc. No. NP_001005743.1) or disheveled (Dvl; the human homologs are at GenBank Acc. No. NM_004421.2 (variant 1); NM_004422.2 (variant 2); and NM_004423.3 (variant 3), both endogenous inhibitors of Notch signalling.

Assaying Differentiation

A variety of methods can be utilized to determine that a stem cell has differentiated into a progenitor cell, or into a cell of the inner ear, e.g., a hair cell or supporting cell. For example, the cell can be examined for the expression of a cell marker gene. Hair cell marker genes include myosin VIIa (myoVIIa), Atoh1, α9 acetylcholine receptor, espin, parvalbumin 3, and Brn3c. Supporting cell markers include claudin14, connexin 26, p75Trk, Notch 1, and S100A. Pluripotent stem cells generally do not express these genes. A stem cell that propagates and produces a cell expressing one or more of these genes, has produced a hair cell, i.e., the stem cell has differentiated at least partially into a hair cell. A stem cell that has differentiated into an inner ear progenitor cell (a precursor of hair cells) expresses early ear marker genes such as nestin, sox2, musashi, Brn3C, Pax2, and Atoh1. A progenitor cell can express one or more of these genes. The progenitor cells can be propagated in serum-free medium in the presence of growth factors. Removal of growth factors and expression of Atoh1, or co-culture with chick otocysts, will induce the cells to differentiate further, such as into hair cells and supporting cells.

Identification of a hair cell or hair cell progenitor (e.g., a hair cell, supporting cell, or progenitor cell that differentiated from a stem cell) can be facilitated by the detection of expression of marker genes as described herein. Detection of the products of gene expression can be by immunocytochemistry. Immunocytochemistry techniques involve the staining of cells or tissues using antibodies against the appropriate antigen. In this case, the appropriate antigen is the protein product of the tissue-specific gene expression. Although, in principle, a first antibody (i.e., the antibody that binds the antigen) can be labeled, it is more common (and improves the visualization) to use a second antibody directed against the first (e.g., an anti-IgG). This second antibody is conjugated either with fluorochromes, or appropriate enzymes for colorimetric reactions, or gold beads (for electron microscopy), or with the biotin-avidin system, so that the location of the primary antibody, and thus the antigen, can be recognized. The protein marker can also be detected by flow cytometry using antibodies against these antigens, or by Western blot analysis of cell extracts.

Alternatively or in addition, gene expression can be analyzed directly, e.g., using PCR methods known in the art, including quantitative PCR, e.g., quantitative RT-PCR, which can be used to detect and compare levels of expression.

Methods of Treatment

The methods described herein can be used to generate cells for therapeutic use. Treatment methods include generating cells of the inner ear (e.g., hair cells or supporting cells) from stem cells, using a method described herein, for transplantation into an ear of a human in need thereof. Transplantation of the cells into the inner ear of a subject can be useful for restoring or improving the ability of the subject to hear, or for decreasing the symptoms of vestibular dysfunction. Inner ear cells derived from stem cells according to the methods described herein need not be fully differentiated to be therapeutically useful. A partially differentiated cell that improves any symptom of a hearing disorder in a subject is useful for the therapeutic compositions and methods described herein.

A human having a disorder of the inner ear, or at risk for developing such a disorder, can be treated with inner ear cells (hair cells or supporting cells) generated from stem cells using a method described herein. In a successful engraftment, at least some transplanted hair cells, for example, will form synaptic contacts with spiral ganglion cells, and integrate into the sensory epithelium of the inner ear. To improve the ability of the cells to engraft, the stem cells can be modified prior to differentiation. For example, the cells can be engineered to overexpress one or more anti-apoptotic genes in the progenitor or differentiated cells. The Fak tyrosine kinase or Akt genes are candidate anti-apoptotic genes that can be useful for this purpose; overexpression of FAK or Akt can prevent cell death in spiral ganglion cells and encourage engraftment when transplanted into another tissue, such as an explanted organ of Corti (see for example, Mangi et al., Nat. Med. 9:1195-201 (2003)). Neural progenitor cells overexpressing $\alpha_v\beta_3$ integrin may have an enhanced ability to extend neurites into a tissue explant, as the integrin has been shown to mediate neurite extension from spiral ganglion neurons on laminin substrates (Aletsee et al., Audiol. Neurootol. 6:57-65 (2001)). In another example, ephrinB2 and ephrinB3 expression can be altered, such as by silencing with RNAi or overexpression with an exogenously expressed cDNA, to modify EphA4 signaling events. Spiral ganglion neurons have been shown to be guided by signals from EphA4 that are mediated by cell surface expression of ephrin-B2 and -B3 (Brors et al., J. Comp. Neurol. 462:90-100 (2003)). Inactivation of this guidance signal may enhance the number of neurons that reach their target in an adult inner ear. Exogenous factors such as the neurotrophins BDNF and NT3, and LIF can be added to tissue transplants to enhance the extension of neurites and their growth towards a target tissue in vivo and in ex vivo tissue cultures. Neurite extension of sensory neurons can be enhanced by the addition of neurotrophins (BDNF, NT3) and LIF (Gillespie et al., NeuroReport 12:275-279 (2001)). A Sonic hedgehog (Shh) polypeptide or polypeptide fragment (e.g., SHH-N), can also be useful as an endogenous factor to enhance neurite extension. Shh is a developmental modulator for the inner ear and a chemoattractant for axons (Charron et al., Cell 113:11 23 (2003)).

Any human experiencing or at risk for developing a hearing loss is a candidate for the treatment methods described herein. For example, the human can receive a transplant of inner ear hair cells or supporting cells generated by a method described herein. A human having or at risk for developing a hearing loss can hear less well than the average human being, or less well than a human before experiencing the hearing loss. For example, hearing can be diminished by at least 5, 10, 30, 50% or more. The human can have sensorineural hearing loss, which results from damage or malfunction of the sensory part (the cochlea) or the neural part (the auditory nerve) of the ear, or conductive hearing loss, which is caused by blockage or damage in the outer and/or middle ear, or the human can have mixed hearing loss, which is caused by a problem in both the conductive pathway (in the outer or middle ear) and in the nerve pathway (the inner ear). An example of a mixed hearing loss is a conductive loss due to a middle-ear infection combined with a sensorineural loss due to damage associated with aging.

The subject can be deaf or have a hearing loss for any reason or as a result of any type of event. For example, a human can be deaf because of a genetic or congenital defect; for example, a human can have been deaf since birth, or can be deaf or hard-of-hearing as a result of a gradual loss of hearing due to a genetic or congenital defect. In another example, a human can be deaf or hard-of-hearing as a result of a traumatic event, such as a physical trauma to a structure of the ear, or a sudden loud noise, or a prolonged exposure to loud noises. For example, prolonged exposures to concert venues, airport runways, and construction areas can cause inner ear damage and subsequent hearing loss. A human can experience chemical-induced ototoxicity, wherein ototoxins include therapeutic drugs including antineoplastic agents, salicylates, quinines, and aminoglycoside antibiotics, contaminants in foods or medicinals, and environmental or industrial pollutants. A human can have a hearing disorder that results from aging, or the human can have tinnitus (characterized by ringing in the ears).

The cells can be administered by any suitable method. For example, to restore hearing, inner ear cells generated by a method described herein can be transplanted, such as in the form of a cell suspension, into the ear by injection, such as into the luminae of the cochlea. See, e.g., the methods described in Corrales et al., J. Neurobiol. 66(13):1489-500 (2006) and Hu et al., Experimental Cell Research 302:40-47 (2005). Injection can be, for example, through the round window of the ear or through the bony capsule surrounding the cochlea. The cells can be injected through the round window into the auditory nerve trunk in the internal auditory meatus or into the scala tympani. In a preferred embodiment, the cells are administered into or near the sensory epithelium of the subject, e.g., into a fluid (perilymph)-filled space above or below the sensory epithelium, i.e., the scala media, scala tympani, or scala vestibuli.

Alternatively, a human suitable for the therapeutic compositions and methods described herein can include a human having a vestibular dysfunction, including bilateral and unilateral vestibular dysfunction. Vestibular dysfunction is an inner ear dysfunction characterized by symptoms that include dizziness, imbalance, vertigo, nausea, and fuzzy vision and may be accompanied by hearing problems, fatigue and changes in cognitive functioning. Vestibular dysfunction can be the result of a genetic or congenital defect; an infection, such as a viral or bacterial infection; or an injury, such as a traumatic or nontraumatic injury. Vestibular dysfunction is most commonly tested by measuring individual symptoms of the disorder (e.g., vertigo, nausea, and fuzzy vision). In these embodiments, the inner ear cells generated by a method described herein can be transplanted, such as in the form of a cell suspension, e.g., by injection, into an organ of the vestibular system, e.g., the utricle, ampulla and sacculus. The cells would generally be injected into the perilymph of these organs or into the vestibule (which connects the 3 organs).

Following treatment with an inner ear cell or inner ear cell progenitor as described herein, the human can be tested for an improvement in hearing or in other symptoms related to inner ear disorders. Methods for measuring hearing are well-known and include pure tone audiometry, air conduction, and bone conduction tests. These exams measure the limits of loudness (intensity) and pitch (frequency) that a human can hear. Hearing tests in humans include behavioral observation audiometry (for infants to seven months), visual reinforcement orientation audiometry (for children 7 months to 3 years) and play audiometry for children older than 3 years. Oto-acoustic emission testing can be used to test the functioning of the cochlear hair cells, and electro-cochleography provides information about the functioning of the cochlea and the first part of the nerve pathway to the brain.

The therapeutic compositions and methods described herein can be used prophylactically, such as to prevent hearing loss, deafness, or other auditory disorder associated with loss of inner ear function. For example, a composition containing a differentiation agent can be administered with a second therapeutic, such as a therapeutic that may effect a hearing disorder. Such ototoxic drugs include the antibiotics neomycin, kanamycin, amikacin, viomycin, gentamycin, tobramycin, erythromycin, vancomycin, and streptomycin; chemotherapeutics such as cisplatin; nonsteroidal anti-inflammatory drugs (NSAIDs) such as choline magnesium trisalicylate, diclofenac, diflunisal, fenoprofen, flurbiprofen, ibuprofen, indomethacin, ketoprofen, meclofenamate, nabumetone, naproxen, oxaprozin, phenylbutazone, piroxicam, salsalate, sulindac, and tolmetin; diuretics; salicylates such as aspirin; and certain malaria treatments such as quinine and chloroquine.

For example, a human undergoing chemotherapy can also be administered an inner ear cell or inner ear cell progenitor as described herein, by a method described herein. The chemotherapeutic agent cisplatin, for example, is known to cause hearing loss. Therefore, a composition containing a differentiation agent can be administered with cisplatin therapy to prevent or lessen the severity of the cisplatin side effect. An inner ear cell or inner ear cell progenitor as described herein can be administered before, after and/or simultaneously with the second therapeutic agent. The two treatments generally will be administered by different routes of administration.

The compositions and methods featured in the invention are appropriate for the treatment of hearing disorders resulting from sensorineural hair cell loss or auditory neuropathy. For example, patients with sensorineural hair cell loss experience the degeneration of cochlear hair cells, which frequently results in the loss of spiral ganglion neurons in regions of hair cell loss, and may also experience loss of supporting cells in the organ of Corti, and degeneration of the limbus, spiral ligament, and stria vascularis in the temporal bone material. Such patients may benefit particularly from administration of supporting cells and/or hair cells into the inner ear.

EXAMPLES

The invention is further described in the following examples, which do not limit the scope of the invention described in the claims.

Example 1: Sensory Progenitors from Mesenchymal Stem Cells

Mesenchymal stem cells were obtained from mouse bone marrow by culturing adherent cells from the marrow under high serum conditions.

Briefly, cells were obtained from bilateral femurs and tibias of 4 week old C57BL/6 or Atoh1-nGFP mice (Helms et al., Development 127, 1185-1196 (2000)) by flushing out the bone marrow with MEM-α (Gibco/BRL) containing 10% fetal bovine serum (FBS; BioWhittaker, Cambrex, N.Y.) and 1 mM glutamine (Gibco/BRL). Pelleted cells were resuspended and mixed with RBC lysis buffer (Gibco/BRL). Approximately $5 \times 10^6$ cells were cultured on a 10 cm dish overnight in MEM-α with 9% horse serum, 9% FBS, 1% Gluta-Max (Invitrogen) and 100 units/ml penicillin and streptomycin (100 µg/ml, Sigma) at 37° C. in a 5% $CO_2$ atmosphere. Nonadherent hematopoietic stem cells were removed, leaving adherent bone marrow stromal cells. When the cells became confluent, trypsinization was performed and the cells were cultured and passaged three to five times, with media changes every 3-4 days. These cells are referred to as mesenchymal stem cells (MSC).

Immunohistochemistry was performed as follows. Cells were fixed for 10 min with 4% paraformaldehyde in PBS. Immunostaining was initiated by rehydrating and blocking the sections for 1 h with 0.1% Triton X-100 in PBS supplemented with 1% BSA and 5% goat serum (PBT1). Fixed and permeabilized cells or rehydrated sections were incubated overnight in PBT1. CD34, CD44, CD45, Sca-1 antibodies (BD Biosciences) diluted 1:40 were used for the characterization of extracted bone marrow cells. Hair cells and bone marrow progenitors were characterized using monoclonal antibody to chick hair cell specific antigen diluted 1:500 (gift from Guy Richardson (Bartolami et al., J Comp Neurol 314, 777-788 (1991)); polyclonal antibody to myosin VIIa, 1:500 (Oshima et al., J Assoc Res Otolaryngol. 8(1):18-31 (2007)); monoclonal antibody to nestin, 1,000 (Developmental Studies Hybridoma Bank, Iowa City, Iowa); polyclonal antibody to parvalbumin 3, 1:2,000 (Heller et al., J Assoc Res Otolaryngol 3, 488-498 (2002)); monoclonal antibody to Atoh1, 1:100 (Developmental Studies Hybridoma Bank); monoclonal antibody to neurofilament M, 1:200 (Chemicon); Polyclonal antibody to collagen type II, 1:40 (Chemicon); polyclonal antibody to Brn3c (Covance, Princeton); Cy-5 conjugated F-actin 1:1000 (Molecular probe). Samples were washed three times for 20 min each with PBS. Anti-rabbit, anti-guinea pig and anti-mouse secondary antibodies conjugated with FITC-, TRITC-, and Cy-5- (Jackson ImmunoResearch) were used to detect primary antibodies. The samples were counterstained with DAPI for 10 min (Vector Laboratories) and viewed by epifluorescence microscopy (Axioskop 2 Mot Axiocam, Zeiss) or confocal microscopy (TCS, Leica). The counting of immunopositive cells was performed by counting 300 cells in 20 randomly selected microscopic fields and significance was calculated by Student's t-test.

Flow cytometric analysis was also performed. MSC were incubated with antibodies to CD34, CD44, CD45 or Sca-1 (BD Biosciences) and further incubated with secondary anti-mouse antibody conjugated to TRITC. Data were acquired and analyzed using an Agilent 2100 Bioanalyzer system and flow cytometry chips (Agilent Technology Inc., Palo Alto, Calif.). The reference window was set so that fluorescence from the secondary antibody alone was less than 2%.

Figure 1B:
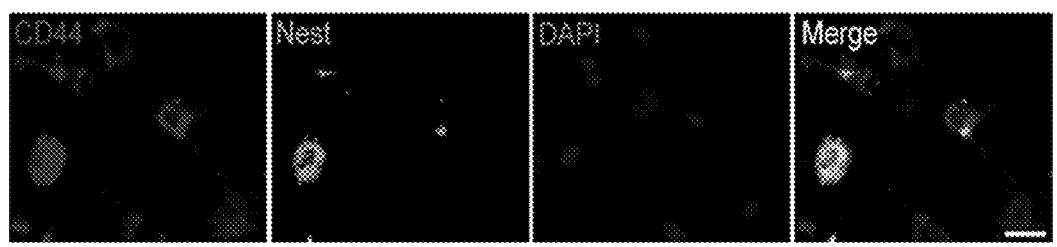
FIG. 1B is a row of four photomicrographs of bone marrow MSCs from passage 3 immunolabeled for CD44 (first panel, medium gray, shown in red in the original) and nestin (second panel, lighter gray, shown in green). The third panel is a DAPI nuclear stain (blue in original). The merged image in the right-most panel shows co-staining of a population of cells with both markers (lightest gray, yellow/orange in the original)
Figure 1C:
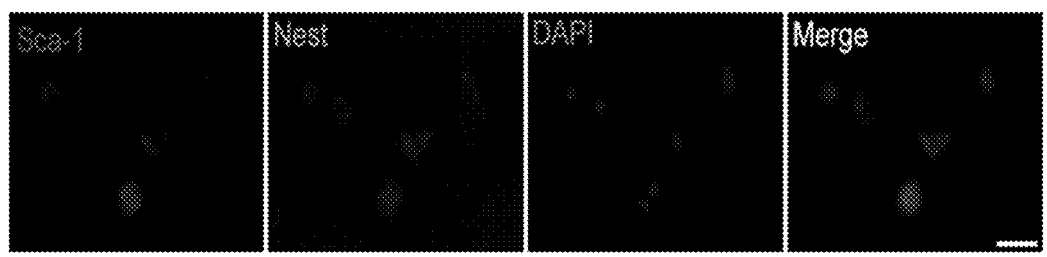
FIG. 1C is a row of four photomicrographs of bone marrow MSCs from passage 3 stained for co-expression of Sca-1 (first panel, red in the original) and nestin (second panel, green in the original). Merged image in the right-most panel shows co-staining.

The MSCs were negative for CD34 and CD45, markers for hematopoietic stem cells in bone marrow (Jiang et al., Nature 418, 41-49 (2002); Pittenger et al., Science 284, 143-147 (1999)) and positive for CD44 and Sca-1, markers for MSCs (Dezawa et al., J Clin Invest 113, 1701-1710 (2004)). Sca-1 was present on 5.2% of the cells and CD44 was present on 11.5% of the cells based on immunohistochemistry and the percentages determined by flow cytometry were similar (FIGS. 1A and 1D and Table 1). We detected co-expression of CD44 and nestin as well as Sca-1 and nestin on a small percentage of the cells (FIGS. 1B and 1C).

TABLE 1

Co-Expression of CD44 and Sca-1 with
Nestin in Mesenchymal Stem Cells

|  | pre-induction (%) | post-induction (%) |
|---|---|---|
| Nestin (+) cells | 4.7 ± 0.8 | 14.2 ± 2.0 |
| CD44 (+) cells | 11.5 ± 1.6 | 11.9 ± 1.8 |
| Sca-1 (+) cells | 5.2 ± 1.5 | 5.0 ± 0.4 |
| CD 44 & nestin (+) cells | 3.4 ± 0.9 | 9.9 ± 0.9 |
| Sca-1 & nestin (+) cells | 2.8 ± 1.2 | 4.3 ± 0.5 |

Positive cells were counted in relation to total nuclei stained by DAPI.
Data are mean ± SE for 10 separate experiments.
The increase in cells staining with nestin was significant ($p < 0.001$) as was the increase in the cells staining for both nestin and CD44 ($p < 0.001$) and nestin and Sca-1 ($p < 0.05$).

We confirmed the previously reported capacity of MSCs to be converted to chondrocytes (Pittenger et al., Science 284, 143-147 (1999)) and neurons (Dezawa et al., J Clin Invest 113, 1701-1710 (2004)). For chondrogenic differentiation, MSC were formed into a micropellet and cultured in DMEM with 10 ng/ml TGFbeta1, 6.25 ug/ml transferrin and 6.25 ug/ml insulin for 2 weeks. Their potential to differentiate into chondrocytes is demonstrated in FIG. 1E. For neuronal differentiation, MSC were cultured in DMEM/F12 1:1 containing N2/B27 supplement with bFGF (10 ng/ml) for 14 days and for 7 days without FGF. This resulted in differentiation to neurons (Dezawa et al., J Clin Invest 113, 1701-1710 (2004)) as shown by neuronal markers (FIG. 1F).

To determine whether otic vesicle growth factors that are important in the early development of inner ear progenitor cells could have a similar effect on MSCs, we removed the serum from the MSCs after 3-5 passages and cultured the cells in serum-free medium containing IGF-1, EGF and bFGF.

For the induction of progenitor cells, passage 3-5 MSC were trypsinized and transferred to 6-well plates or 4 well plates (BD Bioscience) coated with poly-L-ornithine and gelatin or fibronectin (Sigma) at $5 \times 10^4$ cells/ml. Cells were cultured for 5-7 days, and then cultured in serum-free medium composed of DMEM/F12 1:1 containing N2/B27 supplements (Invitrogen). For progenitor cell induction, we used a combination of EGF (20 ng/ml) and IGF (50 ng/ml; R&D Systems, Minneapolis, Minn.) for 2 weeks followed by the addition of bFGF (10 ng/ml) plus the other growth factors for an additional 2 weeks, or a combination of NT3 (30 ng/ml) and bFGF (10 ng/ml) for 4-5 days followed by NT3 (30 ng/ml) and BDNF (10 ng/ml) for 7 days.

Semiquantitative RT-PCR was performed as follows. Total RNA was extracted with the RNAeasy minikit (Qiagen, Valencia, Calif.) according to the manufacturer's instructions. For reverse transcription, 6 μg of total RNA was used with SuperScript III transcriptase (Invitrogen) and oligo-dT primers. The PCR cycling conditions were optimized in pilot experiments. Specific cycling parameters were: initial denaturation step at 94° C. for 2 minutes, denaturation 94° C. for 30 seconds, annealing temperature optimized between 56-60° C. for 30 seconds, extension 72° C. for 60 seconds, extension 72° C. for 60 seconds, and followed by 7 minutes of terminal extension at 72° C. after the last cycle. The number of cycles was optimized between 30 and 35, and conditions were kept constant for each primer. The presented data are from experiments repeated at least 5 times. Control PCR without reverse transcriptase did not produce specific bands. The primer pairs and cDNA product lengths were as follows:

TABLE 2

RT-PCR-Primer Pairs and cDNA Product Length

| cDNA target | Forward primer | SEQ ID NO: | Reverse primer | SEQ ID NO: | Expected product length |
|---|---|---|---|---|---|
| Oct4 | ATG GCT GGA CAC CTG GCT TCA G | 7. | TTA ACC CCA AAG CTC CAG GTT C | 8. | 1033 bp |
| Otx2 | CCA TGA CCT ATA CTC AGG CTT CAG G | 9. | GAA GCT CCA TAT CCC TGG GTG GAA AG | 10. | 211 bp |
| Sox2 | CAC CCG GGC CTC AAC GCT CAC G | 11. | TCC CCT TCT CCA GTT CGC AGT CCA | 12. | 414 bp |
| Pax2 | CCA AAG TGG TGG ACA AGA TTG CC | 13. | GGA TAG GAA GGA CGC TCA AAG AC | 14. | 544 bp |
| Pax6 | AGA CTT TAA CCA AGG GCG GT | 15. | TAG CCA GGT TGC GAA GAA CT | 16. | 589 bp |
| Nestin | AAC AGA GAT TGG AAG GCC GCT GGC | 17. | CTT CAG AAA GGC TGT CAC AGG AG | 18. | 392 bp |
| Musashi | ATG GAG ACT GAC GCG CCC CAG | 19. | ATC TTC TTC GTC CGA GTG AC | 20. | 332 bp |

TABLE 2-continued

RT-PCR-Primer Pairs and cDNA Product Length

| cDNA target | Forward primer | SEQ ID NO: | Reverse primer | SEQ ID NO: | Expected product length |
|---|---|---|---|---|---|
| GATA3 | CCT CCG ACG GCA GGA GTC TTT | 21. | ACC GTA GCC CTG ACG GAG | 22. | 319 bp |
| Math1 | AGA TCT ACA TCA ACG CTC TGT C | 23. | ACT GGC CTC ATC AGA GTC ACT G | 24. | 449 bp |
| Neurogenin-1 | TGG TGT CGT CGG GGA AC | 25. | AAG GCC GAC CTC CAA ACC TC | 26. | 400 bp |
| NeuroD | ACG GGC TGA ACG CGG CGC TGG AC | 27. | TGA AAG AGA AGT TGC CAT TGA TG | 28. | 513 bp |
| Brn3c | GCC ATG CGC CGA GTT TGT C | 29. | ATG GCG CCT AGA TGA TGC | 30. | 714 bp |
| Espin | CAG CCT GAG TCA CCG CAG CCT C | 31. | TGA CCT GTC GCT GCC AGG GCG CG | 32. | 475 bp |
| Myo7a | CTC CCT CTA CAT CGC TCT GTT CG | 33. | AAG CAC CTG CTC CTG CTC GTC CAC G | 34. | 628 bp |
| Zic1 | GGC CAA CCC CAA AAA GTC GTG | 35. | GAG AGC TGG GGT GCG TGT AGG A | 36. | 425 bp |
| Zic2 | GGC GGC GCA GCT CCA CAA CCA GTA | 37. | TTG CCA CAG CCC GGG AAA GGA CAG | 38. | 405 bp |
| TrkB | TTG CCC CTT CCC CTT TTA T | 39. | CGC TTG CTC GCT CTC GT | 40. | 46 bp |
| TrkC | ACC CGC ATC CCA GTC AT | 41. | TCC CGG TGT ACA AAG TGC | 42. | 521 bp |
| P27Kip | CTG GAG CGG ATG GAC GCC AGA C | 43. | CGT CTG CTC CAC AGT GCC AGC | 44. | 525 BP |
| Jag2 | GTC CTT CCC ACA TGG GAG TT | 45. | GTT TCC ACC TTG ACC TCG GT | 46. | |
| Notch1 | AGA GAT GTG GGA TGC AGG AC | 47. | CAC ACA GGG AAC TTC ACC CT | 48. | 306 BP |
| P75 | GTC GTG GGC CTT GTG GCC | 49. | CTG TGA GTT CAC ACT GGG G | 50. | |
| S100 | GCC AAC CGT GTG CTG CTG | 51. | ACG TCG AGA CTG GGC AAG G | 52. | 423 bp |
| Cla14 | CCA GCA CAG CGG | 53. | GGG GCA CGG TTG | 54. | 664 bp |

TABLE 2-continued

RT-PCR-Primer Pairs and cDNA Product Length

| cDNA target | Forward primer | SEQ ID NO: | Reverse primer | SEQ ID NO: | Expected product length |
|---|---|---|---|---|---|
| | TCC AG TAG | | TCC TTG | | |
| Con26 | CGG AAC CAG AGA TAG GAC CTA C | 55. | CTA AGC ACG GGT TGC CTC ATC C | 56. | 824 bp |
| Gapdh | AAC GGG AAG CCC ATC ACC | 57. | CAG CCT TGG CAG CAC CAG | 58. | 442 bp |

Figure 2A:
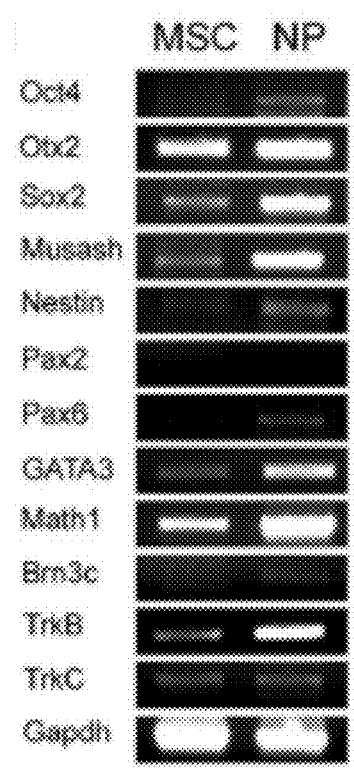
FIG. 2A is a gel showing the results of genetic analysis for neural progenitor markers by RT-PCR of MSCs treated with IGF-1, EGF and bFGF for 14 days followed by analysis. MSC (bone marrow MSCs), NP (neural progenitors at 2 wks after induction of progenitor formation). The genes analyzed are shown to the left of the gel.
Figure 2B:
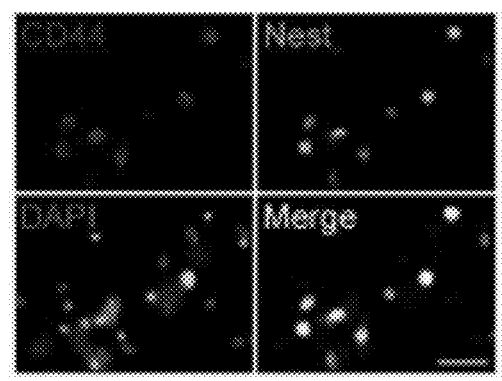
FIGS. 2B-C are two sets of four photomicrographs showing that the neural progenitor marker, nestin, visualized by immunohistochemistry using a secondary antibody labeled with FITC (top right panel in 2B and 2C, shown in green in the original), was co-expressed with CD44 (2B, top left panel, shown in red in the original) and with Sca-1 (2C, top left panel, shown in red in the original). DAPI is shown in blue (lower left panel in each figure). Scale bars are 50 μm. Merged images in the lower right panel of each figure show coexpression of nestin and CD44 (2B) or Sca 1 (2C) (all of the cells appeared green in the original, indicating coexpression).
Figure 2C:
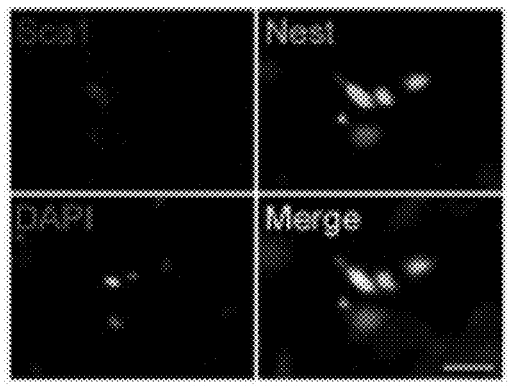

When the expression of neural progenitor cell markers in the resulting cultures was assessed, Otx2, nestin, Sox2, and Musashi were expressed in increased amounts in these cells, which are subsequently referred to herein as progenitor cells, relative to MSCs based on RT-PCR (FIG. 2A). Pax6 was found in the progenitor cells but not in the MSCs (FIG. 2A). Pax2 was not expressed. A low level of Pax5 was detected but Pax8 was not expressed (data not shown). A similar pattern of expression was seen for the stem cell marker, Oct4, which was expressed in the progenitor cells but interestingly, given its role in maintaining the pluripotency of stem cells, was not found in the MSCs. The increase in expression of nestin in the progenitor cells relative to the MSCs (FIG. 2A) was confirmed by immunohistochemistry (FIGS. 2B and 2C and Table 1) and was significant (p<0.001). Additional markers of the hair cell and neural lineages (Atoh1, Brn3c, GATA3) and neuronal markers (TrkB and TrkC) were also expressed in the progenitors (FIG. 2A).

Because of the expression of TrkB and TrkC in the progenitor cell populations, we tested whether incubation with NT-3 and BDNF, the neurotrophins that bind to these receptors, would increase the yield of progenitor cells or alter the expression of genes for hair cell or neuronal fate. We found an increase in expression of Otx2, Sox2, nestin, and Musashi under these conditions as well as an increase in Oct4 expression (FIG. 3A), indicating that the cells may have adopted a neural progenitor cell fate. The neurotrophin-mediated conversion to progenitor cells had a more rapid time course that we found for EGF, IGF-1 and bFGF alone. The expression of proneural transcription factors, NeuroD and Ngn1, as well as neural and hair cell lineage markers, GATA3, Atoh1, and Brn3c, were also increased and the expression of Ngn1 and NeuroD, which select for a neural over a hair cell fate in the inner ear (Kim et al., Development 128, 417-426 (2001); Matei et al., Dev Dyn. 234(3):633-50 (2005)) were higher when NT-3 and BDNF were included in the differentiation medium. Other transcription factors expressed in the otic precursors during development, Zic2 and Pax6, were elevated in the progenitor cells relative to the MSCs, and Zic1 expression was not observed. This suggests that NT-3 and BDNF induced the formation of cells of a neural lineage that were potentially destined to become both neurons and hair cells. However, the cells were not converted to hair cells or neurons because markers for these cells were not found (FIG. 3A, hair cell markers myosin VIIa and espin). We also tested for the expression of genes characteristic of other epithelial cells in the cochlea such as supporting cells, because the progenitors for hair cells can include or give rise to these cells and found that the progenitors expressed S100A, p75$^{trk}$, claudin 14, connexin 26, and Notch1.

The observation of supporting cell markers from the MSC-derived progenitor cells after growth factor induction may be correlated to their origin from a common progenitor during in vivo development (Matei et al., Dev Dyn. 234(3): 633-50 (2005); Satoh and Fekete, Development 132, 1687-1697 (2005)). Since hair cells can be induced to develop from supporting cells after introduction of the Atoh1 gene (Izumikawa et al., Nat Med 11, 271-276 (2005); Zheng and Gao, Nat Neurosci 3, 580-586 (2000)), the role of supporting cells as potential progenitors for hair cells via transdifferentiation has been discussed (Izumikawa et al., Nat Med 11, 271-276 (2005)). The expression of supporting cell genes may reflect an intermediate or accompanying stage on the way to becoming hair cells; in Atoh1 knockout mice undifferentiated cells with markers of supporting cells have been observed to activate the Atoh1 gene (Fritzsch et al., Dev Dyn 233, 570-583 (2005); Woods et al., Nat Neurosci 7, 1310-1318 (2004)). Alternatively, supporting cells could be induced by the developing hair cells: ectopic hair cells in the greater epithelial ridge induced supporting cell markers in surrounding cells (Woods et al., Nat Neurosci 7, 1310-1318 (2004)). The MSCs could be induced to become hair cell progenitors by bFGF, EGF and IGF-1, factors that potentially stimulate the in vivo formation of these progenitors (Leon et al., Endocrinology 136, 3494-3503 (1995); Pauley et al., Dev Dyn 227, 203-215 (2003); Zheng et al., J Neurosci 17, 216-226 (1997)), and these progenitors were able to give rise to hair cells after overexpression of Atoh1. An increase in expression of neural progenitor markers could be caused by expansion of the cells that express these markers or by differentiation of MSCs to the neural progenitor phenotype.

As described herein, MSC-derived progenitor cells expressed neurotrophin receptors. BDNF and NT-3 play important roles in maturation of inner ear neurons (Fritzsch et al., J Neurosci 17, 6213-6225 (1997); Pirvola and Ylikoski, Curr Top Dev Biol 57, 207-223 (2003)), and in differentiation of neural stem cells to neurons (Ito et al., J Neurosci Res 71, 648-658 (2003)), and we therefore tested whether the fate of the progenitors could be modulated by neurotrophins Incubation with these factors resulted in enrichment of progenitors that could be converted to hair cells by subsequent Atoh1 overexpression (Izumikawa et al., Nat Med 11, 271-276 (2005); Zheng and Gao, Nat Neurosci 3, 580-586 (2000)) or co-culture with chick otocyst cells. Since NT-3 and BDNF were found to increase both Atoh1 expression and differentiation in neural stem cells (Ito et al., J Neurosci Res 71, 648-658 (2003)), neurotrophins could directly increase differentiation of MSCs or could increase their competence to respond to overexpressed Atoh1.

Analysis of the progenitor cells obtained from the MSCs revealed parallels with natural development of the inner ear sensory epithelia. The MSC-derived progenitors expressed Sox2, which must be present for subsequent hair cell differentiation in the developing otocyst (Kiernan et al., Nature 434, 1031-1035 (2005)). The expression of Atoh1 in cells that did not have myosin VIIa and the appearance of myosin VIIa at later time points is consistent with the order of their expression during development based on immunohistochemistry (Chen et al., Development 129, 2495-2505 (2002)). The lack of Pax2 expression was surprising since the paired box transcription factor is ubiquitously expressed in the otocyst (Burton et al., Dev Biol 272, 161-175 (2004); Li et al., J Neurobiol 60, 61-70 (2004)). This may suggest that Pax2 is not required or that it can be replaced by another factor for the conversion of MSCs to hair cells. Pax5 was detected and may substitute for Pax2 based on their functional equivalence (Bouchard et al., Development. 127(5): 1017-28 (2000)). This is consistent with the analysis of the Pax2 null mouse (Burton et al., Dev Biol 272, 161-175 (2004)), which appears to develop hair cells despite severe disruption of the normal morphology of the cochlea. The lack of Zic1 expression relative to Zic2 is also found during development of a hair cell phenotype as compared to sensory neurons in the otocyst (Warner et al., Dev Dyn 226, 702-712 (2003)) and is thus consistent with the development of a hair cell phenotype. The identification of inductive molecules on chick otocyst cells that are not present in conditioned media will provide further insights into hair cell differentiation.

The isolation of progenitor cells that can give rise to the tissue of origin, as observed in the inner ear (Li et al., Trends Mol Med 10, 309-315 (2004); Li et al., Nat Med 9, 1293-1299 (2003a)), might be predicted and yet the cells do not regenerate after damage, possibly because of the decrease in number of inner ear stem cells after birth (Oshima et al., J Assoc Res Otolaryngol. 8(1):18-31 (2007)). Therefore, a source of cells to provide replacements for these sensory cells is highly desirable. The in vivo role of MSCs in regeneration generally remains uncertain although bone marrow could act as a source of new cells in organs with few progenitors. Despite the demonstration that cells from bone marrow migrate into the brain and heart in adults (Oshima et al., J Assoc Res Otolaryngol. 8(1):18-31 (2007)); Weimann et al., Proc Natl Acad Sci USA 100, 2088-2093 (2003)) and differentiate into neurons in the brain, hematopoietic stem cells from bone marrow were not converted to cardiomyocytes after injection (Murry et al., Nature 428, 664-668 (2004)) and conversion to neurons was extremely rare (Wagers et al., Science 297, 2256-2259 (2002); Weimann et al., Proc Natl Acad Sci USA 100, 2088-2093 (2003)). The most successful attempts at regeneration by adult stem cells from other tissues have been obtained after a lesion Doyonnas et al., Proc Natl Acad Sci USA 101, 13507-13512 (2004); Edge, Transplant Proc 32, 1169-1171 (2000); Hess et al., Nat Biotechnol 21, 763-770 (2003); Pagani et al., J Am Coll Cardiol 41, 879-888 (2003)) and tissue damage may be required to see cell replacement by bone marrow-derived cells. Whether bone marrow-derived cells play any regenerative role in the sensory or peripheral nervous system in a spontaneous response to damage in vivo is an unanswered question, but, although low-level replacement of hair cells by bone marrow cells in vivo cannot be ruled out, spontaneous replacement of sensory cells is unlikely to be significant given the lack of hair cell regeneration seen in the adult cochlear and vestibular systems (Hawkins and Lovett, Hum Mol Genet 13(Spec No 2):R289-296 (2004); White et al., Nature 441, 984-987 (2006)).

Example 2: Transfection with an Atoh1 Expression Plasmid Converts Progenitors to Hair Cells To test whether the progenitor cells could act as inner ear precursor cells, it was evaluated whether overexpression of Atoh1, a transcription factor that is known to push competent progenitors to a hair cell fate (Izumikawa et al., Nat Med 11, 271-276 (2005); Zheng and Gao, Nat Neurosci 3, 580-586 (2000)), would increase the expression of hair cell markers.

The efficiency of Atoh1 transfection was tested by counting green fluorescent cells after transfection with a vector coding for GFP expression in addition to Atoh1. We constructed a vector containing the Atoh1 coding sequence under EF1alpha-promotor control in the pTracer-EF vector (Invitrogen) that has a GFP-Zeocin fusion sequence under the CMV promoter. Gene transfection was done in the progenitor cell state or as MSC using LIPOFECTAMINE™ transfection reagent (Sigma). Cells were cultured in Zeocin (Invitrogen) to obtain stable transfectants. Transfected MSC were cultured in the serum-free conditions with combinations of growth factors.

Figure 4A:
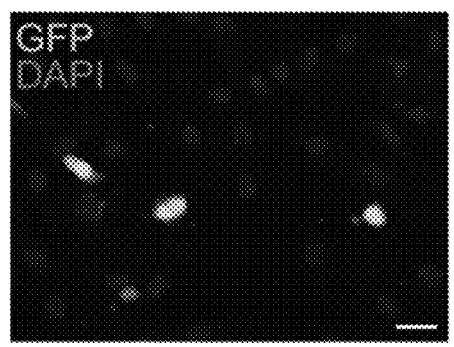
FIG. 4A is a photomicrograph showing exogenous expression of Atoh1 in bone marrow MSCs; expression was observed in cells and nuclei (green in the original) due to the expression of GFP from the vector.
Figure 4B:
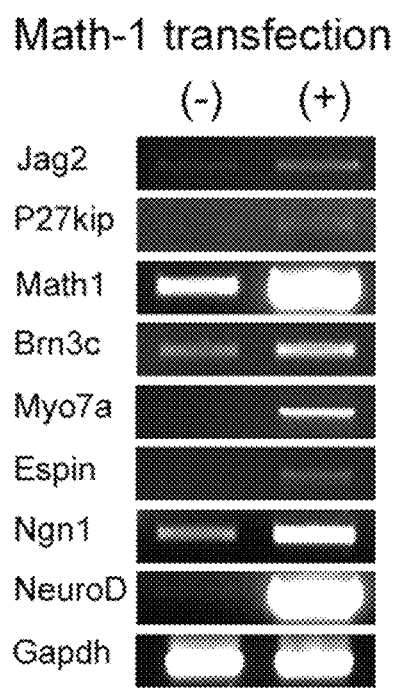
FIG. 4B is a gel showing the results of gene expression in cells transfected with Atoh1 followed by treatment of the cells with NT3, FGF and BDNF. The results indicate that this protocol gave rise to progenitor cells that subsequently matured into cells expressing hair cell genes, including espin, myosin Vila, jagged 2, and Brn3c, and p27Kip, in addition to the proneural genes, Ngn1 and NeuroD.
Figure 4C:
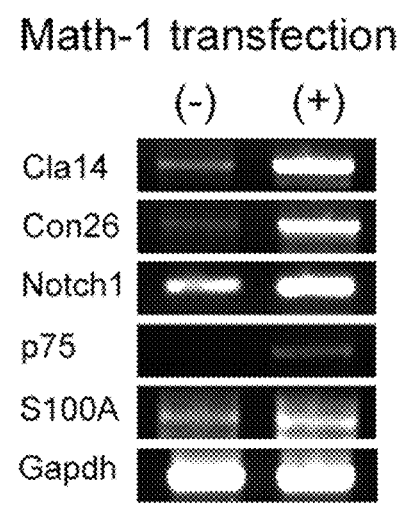
FIG. 4C is a gel showing the results of further genetic analysis of the cells under the differentiating conditions described in 4B; the results showed that the cells also expressed S100A, $p75^{Trk}$, claudin 14, connexin 26, and Notch1, consistent with some cells having a supporting cell phenotype.
Figure 4D:
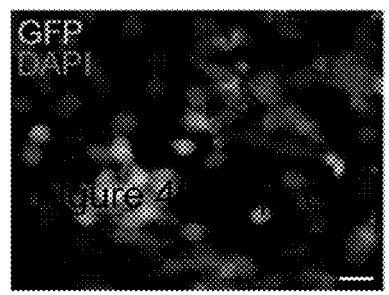
FIG. 4D is a photomicrograph of an MSC cell line selected in Zeocin; the cells had a high percentage of GFP expression when cultured in serum (green in original).
Figure 4E:
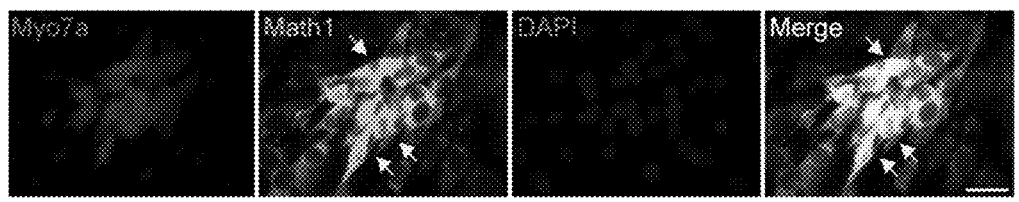
FIG. 4E is a row of 4 photomicrographs of cells stained for Myo7a (first panel), Math1/Atoh1 (second panel), or DAPI (third panel); the last panel is a merged image. After differentiation, the number of hair cell-like cells per DAPI nucleus rose and these cells stained for myosin VIIa (shown in red in the first panel) and Atoh1 (shown in green in the second panel; arrows in the second and last panels).
Figure 4F:
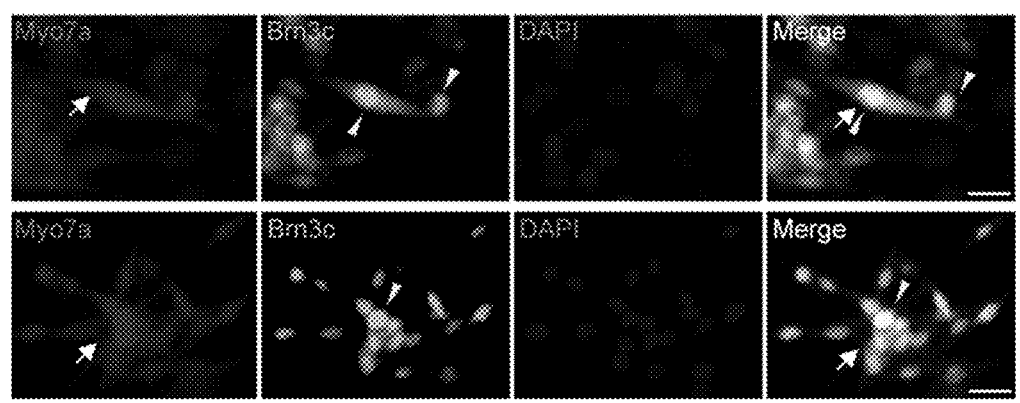
FIG. 4F is two rows of 4 photomicrographs of an Atoh1 expressing cell line differentiated to cells with nuclei that were immunopositive for Brn3c (second column, green in original; indicated by arrowheads) and cytoplasm positive for myosin VIIa (first column, red in original; indicated by arrows). Nuclei were stained with DAPI (third column, blue in original).
Figure 4G:
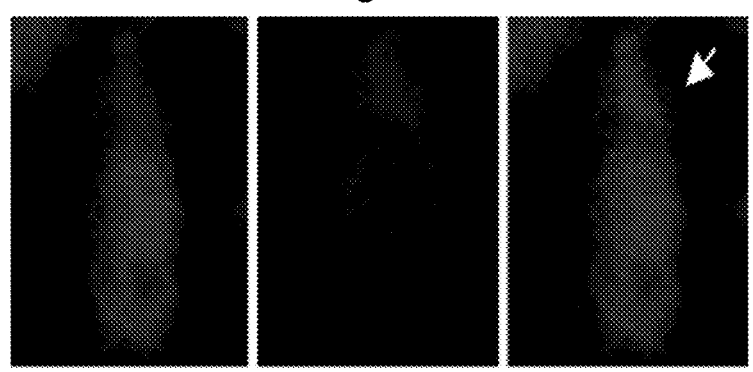
FIG. 4G is a row of three photomicrographs showing that the differentiated cells were positive for F-actin which protruded from the apex of the cell in the shape of a stereocilia bundle (arrow).
Figure 4H:
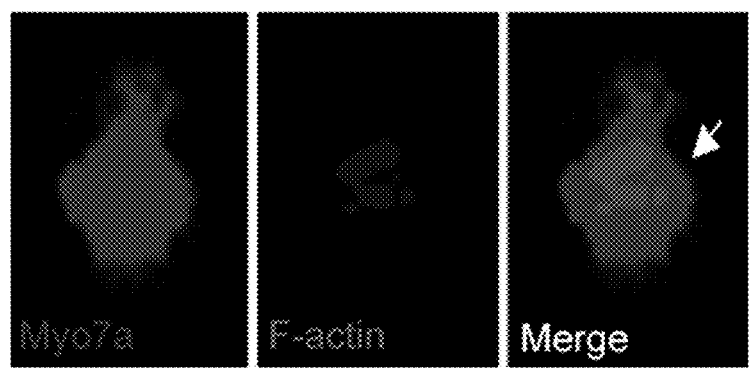
FIG. 4H is a row of three photomicrographs showing that F-actin staining was arranged in a characteristic V pattern on the apical surface.

When MSCs were transfected, as many as 2% of the cells were GFP positive at 24 hours (FIG. 4A). RT-PCR at day 14 showed that the transfected cell population expressed markers of developing sensory epithelia, such as p27Kip, Brn3c and jagged2, and mature hair cells markers, myosin VIIa and espin (FIG. 4B) as well as increased expression of Ngn1 and NeuroD. We also detected expression of supporting cell markers, S100A, $p75^{Trk}$, claudin 14, connexin 26, and Notch1, indicating that the progenitor cells could give rise to hair cells and supporting cells (FIG. 4C). Selection of MSC transfectants with stable Atoh1 expression increased the percentage of GFP-positive cells (FIG. 4D). Incubation of these cells in the growth factors described above followed by immunohistochemistry yielded cells with expression of Atoh1 and myosin VIIa respectively in 7.7% and 7.1% of the total cells (FIG. 4E). Differentiation under growth factor stimulation gave rise to cells with Brn3c in the nucleus and myosin VIIa in the cytoplasm (FIG. 4F). These cells were positive for both markers in the same cells, with 92% of the Atoh1-positive cells showing staining for myosin VIIa, and 77% of the Brn3c-positive cells showing staining for myosin VIIa. Examination of the myosin VIIa positive cells for F-actin (FIGS. 4G and H) indicated that some of the cells (4.9% of the myosin VIIa-positive cells) had developed protrusions at their apical poles. These protrusion had the polarized appearance of stereociliary bundles and were positive for espin (FIG. 4G).

Atoh1 expression led to strong expression of helix-loop-helix transcription factors, Ngn1 and NeuroD. Several previous studies have indicated that Atoh1 expression can increase these transcription factors. In mouse cerebellum Atoh1 expression leads to overexpression of NeuroD (Helms et al., Mol Cell Neurosci 17, 671-682 (2001)). In zebrafish NeuroD is not expressed in the absence of Atoh1 (Sarrazin et al., Dev Biol 295, 534-545 (2006)) and is required for hair cell formation. The related mouse achaete-scute (Mash1) upregulates Ngn1 (Cau et al., Development 124, 1611-1621 (1997)). However, Ngn1 was downregulated by overexpression of Atoh1 in chick neural tube (Gowan et al., Neuron 31, 219-232 (2001)).

These data demonstrate that overexpression of Atoh1 in growth-factor induced progenitor cells induces the differentiation of a percentage of those cells to hair cells.

Example 3: Conversion of Progenitors to Hair Cells is Stimulated by Developing Otocyst Cells To test whether the developing otocyst produced factors that would increase the differentiation of MSCs to hair cells, co-culture experiments of E3 chick otocyst cells with MSCs were performed.

Embryos of the white leghorn strain (Charles River) were harvested 72 hours after placing fertilized eggs onto rocking platforms in a humidified incubator maintained at 38° C. The dissection of otocysts from the extracted embryos was done in cooled PBS, pH 7.2, after removal of periotic mesenchymal tissues. The otocysts were trypsinized and dissociated to single cells for plating and $2 \times 10^4$ cells were cultured overnight in four-well plates in 10% FBS. One day after plating, the otocyst cells were fixed with 4% paraformaldehyde for 20 minutes, or inactivated with mitomicin C (10 µg/ml) for 3 hours, then washed 4 times with PBS. Conditioned medium from the cultured cells was collected and frozen prior to use on progenitors cells. Progenitor cells ($5 \times 10^4$ cells/ml) induced in serum-free medium with growth factors, were overlaid on the chick otocyst cells and cultured for 5-7 days with EGF/IGF, followed by 10 days with EGF/IGF/FGF and withdrawal of growth factors for 5-10 more days. The cells were analyzed by RT-PCR or immunohistochemistry as described herein.

Figure 5A:
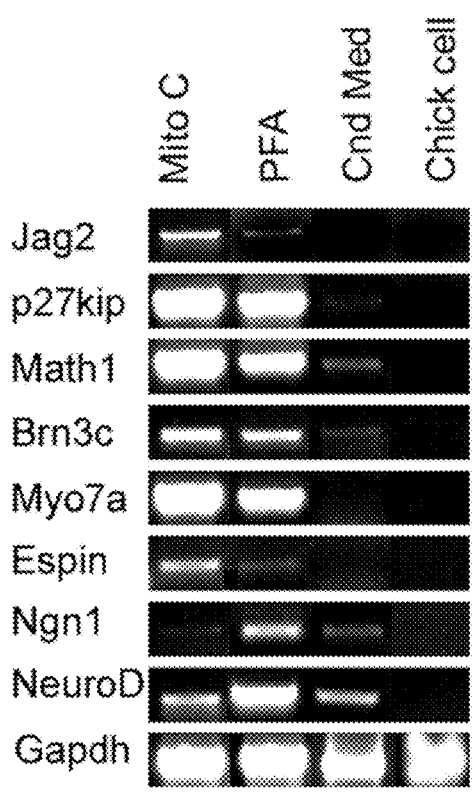
FIG. 5A is a gel showing the results of genetic analysis of bone marrow MSC derived progenitors were co-cultured for 21 days with chick otocyst cells that had been treated with mitomycin C (Mito C); the results showed that expression of jagged 2, p27Kip, Atoh1, Brn3c, myosin VIIa and espin was increased, whereas the expression of these genes in chick cells was undetectable. Chick otocyst cells that had been fixed by incubation with paraformaldehyde were less effective (PFA) than the unfixed cells but did cause differentiation of the progenitors. Conditioned medium from the chick cells (Cnd Med) had no effect (levels of expression of these markers similar to previously shown data for differentiating conditions).
Figure 5B:
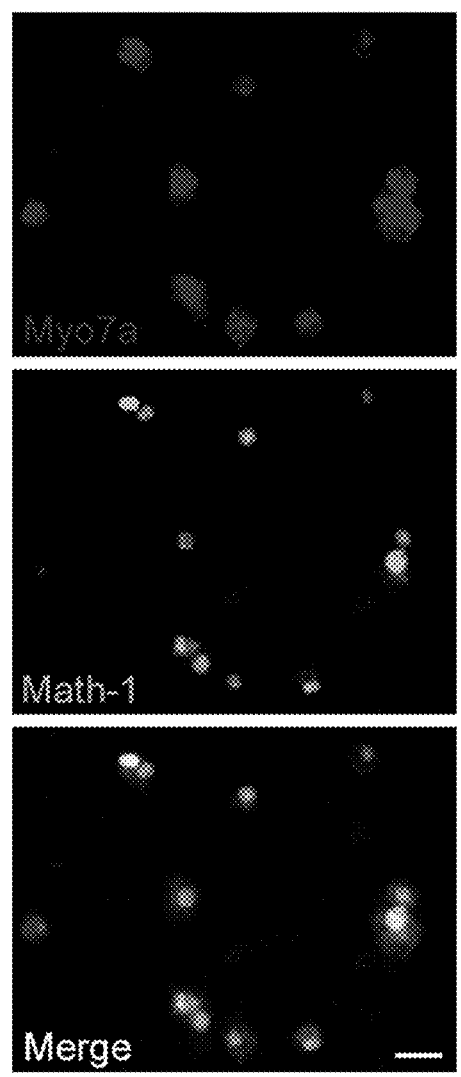
FIG. 5B is a set of three photomicrographs showing that expression of Atoh1 (Math-1, middle panel, green in original) and myosin VIIa (top panel, red in original) in cells from a Atoh1-GFP mouse showed green fluorescence corresponding to the induction of this marker in the nucleus and had expression of myosin VIIa in the cytoplasm.

After culture in the presence of the chick otocyst cells for 21 days, increased expression of myosin VIIa, jagged2, p27Kip, Brn3c and Atoh1 by RT-PCR was found (FIG. 5A). The factor(s) was unlikely to be a secreted molecule because fixation of the cells did not diminish their ability to promote differentiation after exposure for 14 days, while conditioned medium was ineffective in 14 days (FIG. 5A). Conversion of the stem cells to hair cells could be followed by appearance of green fluorescence in the cultures using MSCs derived from transgenic Atoh1-nGFP mice that express a nuclear version of enhanced GFP when Atoh1 enhancer elements are activated (Chen et al., Development 129, 2495-2505 (2002); Lumpkin et al., Gene Expr Patterns 3, 389-395 (2003)). These green cells were observed in the co-cultures with chick otocyst cells (FIG. 5B) and the cells were co-labeled with antibody to myosin VIIa.

The otocyst from E3 chick embryos were used for injection of progenitor cells. The dissected otocysts were transferred into 7 ml of serum-free DMEM/F12 1:1 containing N2 and B27 on a gelatin-coated tissue culture dish. After attachment of intact otocysts, progenitor cells from MSC ($5 \times 10^7$ cells/ml) were injected into the otocyst with a micropipette in 2 µl of medium. The left otic vesicles did not receive cell grafts and served as controls. The otocysts were harvested after 10-14 days, fixed 30 min in paraformaldehyde (4% in PBS), cryoprotected overnight in sucrose (30% in PBS), embedded in TissueTek (EMS) and serially sectioned (16 µm) with a cryostat (CM3050, Leica, Nussloch, Germany).

Figure 6A:
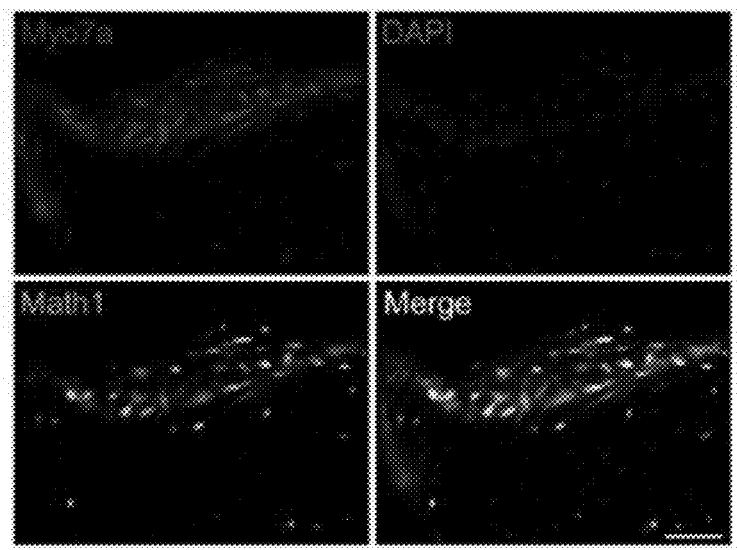
FIG. 6A is a set of four photomicrographs showing an increase in fluorescence (green in original) indicating the conversion of bone marrow cells to cells expressing Atoh1. The cells stained for Atoh1 (Math1, bottom left, green in original), myosin VIIa (top left, red in original) and DAPI (top right, blue in original). A merged image is shown in on the bottom right panel.
Figure 6B:
FIG. 6B is a photomicrograph showing that Atoh1-expressing cells were found incorporated into the tissue of the chick otic epithelium. The hair cells of the chick were stained with the chick-specific marker, HCA (white in original) and myosin VIIa (red in original), whereas the Atoh-1 expressing mouse cells were green due to expression of GFP (arrows).
Figure 6C:
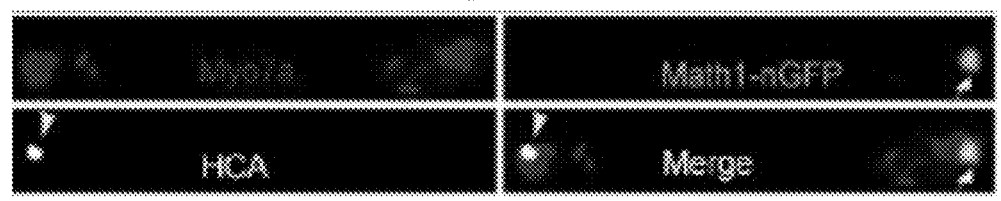
FIG. 6C is a set of four photomicrographs showing a lack of cell fusion, demonstrated by the presence of HCA (arrowhead, lower panels) in cells that did not have green fluorescence and of Atoh1-GFP (arrow, right column) exclusively in cells that did not stain for HCA, a marker for chicken cells. No cells with both GFP and HCA were observed in these experiments. Scale bars are 100 µm.

When the progenitor cells were injected into chick otocysts obtained at E3, conversion of progenitors to cells with hair cell properties (5% of the myosin VIIa-positive cells were positive for nGFP) was observed (FIG. 6A). The murine hair cells were seen to incorporate into the hair cell bearing epithelia of the developing chicken otocyst as detected by expression of GFP (FIG. 6B). One possible explanation for the expression of hair cell genes by the MSC-derived cells in co-culture is fusion with chick cells. To rule this out we labeled the cells with an antibody to chick hair cell antigen (Bartolami et al., J Comp Neurol 314, 777-788 (1991)). Native chick hair cells could be detected lining the internal cavity of the otocyst (51% of 1,352 cells from 15 otocyst injections that stained for myosin VIIa were positive for chick hair cell antigen), and the cells that expressed nGFP and hair cell markers did not co-express chick hair cell antigen (FIG. 6C) and were therefore of mouse origin and not the product of cell fusion.

These experiments, performed in an attempt to understand how contact of the MSCs with developing otocyst cells provided a signal that induced their differentiation to hair cells, demonstrated that the inductive effect was through a cell surface molecule as opposed to a secreted factor. Injection of the MSC into the developing otocyst in vitro indicated that hair cells that differentiated from the stem cells were integrated into the chick otocyst epithelium, demonstrating that the environment provided by developing chicken otocyst cells could guide differentiation and integration of suitable progenitor cells. The instructive influence has also been seen previously with inner ear-derived stem cells and murine ES cell-derived progenitor cells (Li et al., Trends Mol Med 10, 309-315 (2004); Li et al., Nat Med 9, 1293-1299 (2003); Li et al., Proc Natl Acad Sci USA 100, 13495-13500 (2003).

The effect of the co-incubation with otocyst cells may be simply to activate Atoh1 expression and a sufficient amount of Atoh1 may be required to allow hair cell differentiation since the MSCs had low levels of Atoh1 but did not have detectable sensory epithelial cell markers. This type of high level expression could be needed for Atoh1 to overcome the level of preexisting endogenous inhibitors that interact with Atoh1 protein. The murine cells could be clearly distinguished from the chick hair cells that differentiated at the same time by their expression of nGFP and by immunolabeling of the chick hair cells with a species-specific antibody. The cells were never co-stained (based on examination of 1,352 cells), indicating that the mouse hair cells had differentiated from stem cells and did not arise from cell fusion.

Example 4: Inhibition of Notch Signaling Induces Differentiation of Hair Cells

The Notch pathway maintains the alternating pattern of hair cells and supporting cells in vivo by suppressing the differentiation of hair cells from supporting cells and activation of Notch in the embryo appears to block development of hair cells from progenitors.

Figure 7:
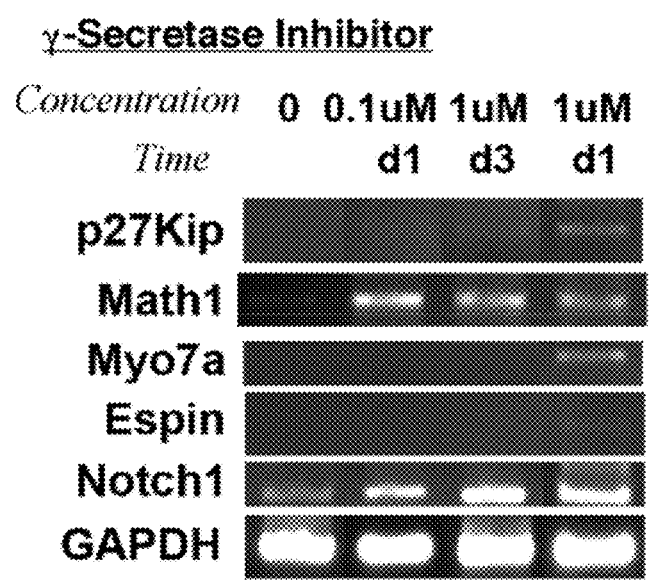
FIG. 7 is a gel showing the results of genetic analysis of cells after inhibition of Notch signaling with an inhibitor of γ-secretase increases expression of hair cell markers. Gene expression in MSCs treated with a γ-secretase inhibitor showed that loss of Notch signaling increased Atoh1 expression. The timing of inhibition was critical: γ-secretase inhibitor added at d1 of differentiation in vitro for a total of 10 days led to an increase in hair cell markers, myosin VIIa and espin, whereas inhibitor added at d3 did not induce hair cell markers.

To examine the effect of the Notch pathway on the differentiation of hair cells, the NT3/BDNF treated progenitors were incubated with a γ-secretase inhibitor. Analysis of gene expression in the progenitors made by incubation with NT3, BDNF, FGF and subsequently treated with the γ-secretase inhibitor demonstrated that loss of the notch signaling increased Atoh1 expression. Atoh1 levels rose compared to the treatment with growth factors alone based on RT-PCR when the inhibitor was used at 1 µM (FIG. 7). The timing of the addition of the inhibitor was essential with inhibition at a later stage (after 3 days of differentiation in vitro) causing less induction of hair cell markers than inhibition starting at day 0 and continuing for 10 days. At the low concentration, γ-secretase inhibitor activates ngn1 and NeuroD and causes no increase in Atoh1 or hair cell markers. At higher concentration, the γ-secretase inhibitor increases Atoh1 and Brn3c expression. The increased Atoh1 appeared to be able to produce hair cells as the cells expressed markers for the hair cells such as myosin7a, p27Kip. As HLH transcription factors mediate the effects of the Notch pathway, this result is consistent with the role of Notch and suggests a mechanism for preventing hair cell differentiation under normal conditions.

Example 5: Inhibition of Hair Cell Differentiation in Human Stem Cells

To determine if human mesenchymal stem cells (hMSCs) can be differentiated into inner ear cell types including hair cells or sensory neurons, human bone marrow cells from healthy adults were evaluated.

The human bone marrow cells were harvested and cultured as plated on tissue culture plastic for 16 hours, and nonadherent hematopoietic stem cells were aspirated.

First, the adherent cells were cultured in αMEM containing 9% horse serum and 9% fetal bovine serum and were negative for blood-forming cell markers, CD34 and CD45. These cells gave rise to chondrocytes expressing type II and IV collagen after culture in the presence of TGFβ, transferrin and insulin.

Culture of hMSCs in DMEM/F12 medium containing N2 and B27 without serum in the presence of NT-3, BDNF, Sonic hedgehog and retinoic acid for 10 days gave rise to cells that expressed neurosensory progenitor markers detected by RT-PCR, Musashi, nestin, Pax6, Brn3a, NeuroD, Ngn1, and GATA3, and sensory neuron markers, peripherin and TrkC. These differentiated hMSCs were positive for β-III tubulin (2.1% of the total cells were positive based on immunohistochemistry) and, of these cells, 28% co-stained for peripherin and 31% co-stained for Brn3a.

For the differentiation to hair cells, hMSCs were transfected with human Atoh1 in an expression vector with a selectable marker for eukaryotic cells. The selected progenitor cells expressed Atoh1 and, after differentiation in DMEM/F12 medium containing N2 and B27 with NT-3 and BDNF for 10 days, expressed hair cell markers, Atoh1, myosin VIIa, p27Kip, Jag2 and espin based on RT-PCR.

The ability of these cells to engraft in an organ of Corti, the Atoh1-transfected cells were co-cultured with an ex vivo organ of Corti from mouse. This gave rise to cells expressing myosin VIIa and espin that were detected by immunostaining, i.e., differentiated hair cells. When the ex vivo mouse organ of Corti was treated with toxins to induce hair cell degeneration, co-cultured bone marrow-derived cells were observed to engraft in the mouse sensory epithelium, thus demonstrating the ability of cells obtained.

Thus, human MSCs are a potential alternative for cell-based treatment of hearing loss, as they can be differentiated into inner ear cell types including hair cells or sensory neurons, and can be successfully engrafted into structures of the inner ear.

Example 6: Math1-Estrogen Receptor (ER) Fusion Constructs

One alternative to constitutive expression of Math1 is to use a conditional or inducible system of gene expression, to upregulate Math1 with an inducer that is added to the cell medium or cochlear environment. An inducible model is particularly useful when investigating the temporal effects of gene expression.

This Example describes a system in which administration of tamoxifen, a synthetic estrogen agonist, induces expression of Math1. A Math1-estrogen receptor (ER) fusion protein, where the ER has been mutated so that it selectively binds to tamoxifen rather than estrogen, is constitutively expressed. In the absence of tamoxifen, the Math1-ER construct remains quiescent within the cytosol where it is inactivated by heat shock proteins. The addition of tamoxifen to the transfected cells results in a dose-dependent localization of the Math1-ER construct to the nucleus where it is transcribed leading to increased expression of Math1. The sequence of Math1 is given above.

The sequence of ER used is as follows (SEQ ID NO:59):

ATGTCCAATTTACTGACCGTACACCAAAATTTGCCTGCATTACCGGTCGA

TGCAACGAGTGATGAGGTTCGCAAGAACCTGATGGACATGTTCAGGGATC

GCCAGGCGTTTTCTGAGCATACCTGGAAAATGCTTCTGTCCGTTTGCCGG

TCGTGGGCGGCATGGTGCAAGTTGAATAACCGGAAATGGTTTCCCGCAGA

ACCTGAAGATGTTCGCGATTATCTTCTATATCTTCAGGCGCGCGGTCTGG

CAGTAAAAACTATCCAGCAACATTTGGGCCAGCTAAACATGCTTCATCGT

CGGTCCGGGCTGCCACGACCAAGTGACAGCAATGCTGTTTCACTGGTTAT

GCGGCGGATCCGAAAAGAAAACGTTGATGCCGGTGAACGTGCAAAACAGG

CTCTAGCGTTCGAACGCACTGATTTCGACCAGGTTCGTTCACTCATGGAA

AATAGCGATCGCTGCCAGGATATACGTAATCTGGCATTTCTGGGGATTGC

TTATAACACCCTGTTACGTATAGCCGAAATTGCCAGGATCAGGGTTAAAG

ATATCTCACGTACTGACGGTGGGAGAATGTTAATCCATATTGGCAGAACG

AAAACGCTGGTTAGCACCGCAGGTGTAGAGAAGGCACTTAGCCTGGGGGT

AACTAAACTGGTCGAGCGATGGATTTCCGTCTCTGGTGTAGCTGATGATC

CGAATAACTACCTGTTTTGCCGGGTCAGAAAAAATGGTGTTGCCGCGCCA

TCTGCCACCAGCCAGCTATCAACTCGCGCCCTGGAAGGGATTTTTGAAGC

AACTCATCGATTGATTTACGGCGCTAAGGATGACTCTGGTCAGAGATACC

TGGCCTGGTCTGGACACAGTGCCCGTGTCGGAGCCGCGCGAGATATGGCC

CGCGCTGGAGTTTCAATACCGGAGATCATGCAAGCTGGTGGCTGGACCAA

TGTAAATATTGTCATGAACTATATCCGTAACCTGGATAGTGAAACAGGGG

CAATGGTGCGCCTGCTGGAAGATGGGGATCAGGCTGGTGCCATGGGCGAT

CCACGAAATGAAATGGGTGCTTCAGGAGACATGAGGGCTGCCAACCTTTG

GCCAAGCCCTCTTGTGATTAAGCACACTAAGAAGAATAGCCCTGCCTTGT

CCTTGACAGCTGACCAGATGGTCAGTGCCTTGTTGGATGCTGAACCGCCC

ATGATCTATTCTGAATATGATCCTTCTAGACCCTTCAGTGAAGCCTCAAT

GATGGGCTTATTGACCAACCTAGCAGATAGGGAGCTGGTTCATATGATCA

ACTGGGCAAAGAGAGTGCCAGGCTTTGGGACTTGAATCTCCATGATCAG

GTCCACCTTCTCGAGTGTGCCTGGCTGGAGATTCTGATGATTGGTCTCGT

CTGGCGCTCCATGGAACACCCGGGGAAGCTCCTGTTTGCTCCTAACTTGC

TCCTGGACAGGAATCAAGGTAAATGTGTGGAAGGCATGGTGGAGATCTTT

GACATGTTGCTTGCTACGTCAAGTCGGTTCCGCATGATGAACCTGCAGGG

TGAAGAGTTTGTGTGCCTCAAATCCATCATTTTGCTTAATTCCGGAGTGT

-continued

```
ACACGTTTCTGTCCAGCACCTTGAAGTCTCTGGAAGAGAAGGACCACATC

CACCGTGTCCTGGACAAGATCACAGACACTTTGATCCACCTGATGGCCAA

AGCTGGCCTGACTCTGCAGCAGCAGCATCGCCGCCTAGCTCAGCTCCTTC

TCATTCTTTCCCATATCCGGCACATGAGTAACAAACGCATGGAGCATCTC

TACAACATGAAATGCAAGAACGTGGTACCCCTCTATGACCTGCTCCTGGA

GATGTTGGATGCCCACCGCCTTCATGCCCCAGCCAGTCGCATGGGAGTGC

CCCCAGAGGAGCCCAGCCAGACCCAGCTGGCCACCACCAGCTCCACTTCA

GCACATTCCTTACAAACCTACTACATACCCCCGGAAGCAGAGGGCTTCCC

CAACACGATCTGA
```

ADDITIONAL REFERENCES

Kicic et al., J Neurosci 23, 7742-7749 (2003).
Ma et al., J Assoc Res Otolaryngol 1, 129-143 (2000).
Wang et al., Nature 422, 897-901 (2003).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An in vitro method of generating a differentiated inner ear auditory hair cell, the method comprising:
   (i) providing a population of mesenchymal stem cells obtained from mammalian bone marrow;
   (ii) culturing the mesenchymal stem cell in serum-free medium containing insulin-like growth factor-1 (IGF-1), epidermal growth factor (EGF), and basic fibroblast growth factor (bFGF);
   (iii) inducing the stem cell by maintaining said cell in medium comprising neurotrophin-3 (NT-3) and brain derived neurotrophic factor (BDNF) for time sufficient to differentiate into a progenitor cell that expresses Sox2, Pax6, nestin, and musashih; and
   (iv) culturing the progenitor cell in the presence of a gamma secretase inhibitor in an amount and for a time sufficient to produce a differentiated inner ear auditory hair cell that expresses myosin VIIa, and espin and optionally expresses one or both of atonal homolog 1 (Atoh1) or jagged 2,
   thereby producing a differentiated inner ear auditory hair cell, wherein the gamma secretase inhibitor is selected from the group consisting of an arylsulfonamide, a dibenzazepine, a benzodiazepine, N—[N-(3,5-difluorophenacetyl)-L-alanyl]-(S)-phenylglycine t-butyl ester (DAPT), L-685,458, and MK0752.

2. The method of claim 1, wherein the mesenchymal stem cell is obtained from a subject who has sensorineural hair cell loss.

3. The method of claim 1, wherein the inner ear auditory hair cell expresses Atoh1, myosin7a, and epsin.

* * * * *

UNITED STATES PATENT AND TRADEMARK OFFICE
CERTIFICATE OF CORRECTION

PATENT NO. : 9,896,658 B2
APPLICATION NO. : 14/833919
DATED : February 20, 2018
INVENTOR(S) : Albert Edge Page 1 of 1

It is certified that error appears in the above-identified patent and that said Letters Patent is hereby corrected as shown below:

On the Title Page

Column 1 (Assignee), Line 1, delete "Eat" and insert -- Ear --,

In the Claims

In Column 59, Line 48 (approx.), in Claim 1, delete "musashih;" and insert -- musashi; --.

Signed and Sealed this
Twenty-second Day of May, 2018

Andrei Iancu
*Director of the United States Patent and Trademark Office*

SEQUENCE LISTING

```
<160> NUMBER OF SEQ ID NOS: 59

<210> SEQ ID NO 1
<211> LENGTH: 1065
<212> TYPE: DNA
<213> ORGANISM: Homo sapiens

<400> SEQUENCE: 1
atgtcccgcc tgctgcatgc agaagagtgg gctgaagtga aggagttggg agaccaccat      60
cgccagcccc agccgcatca tctcccgcaa ccgccgccgc cgccgcagcc acctgcaact     120
ttgcaggcga gagagcatcc cgtctacccg cctgagctgt ccctcctgga cagcaccgac     180
ccacgcgcct ggctggctcc cactttgcag ggcatctgca cggcacgcgc cgcccagtat     240
ttgctacatt ccccggagct gggtgcctca gaggccgctg cgccccggga cgaggtggac     300
ggccgggggg agctggtaag gaggagcagc ggcggtgcca gcagcagcaa gagccccggg     360
ccggtgaaag tgcgggaaca gctgtgcaag ctgaaaggcg gggtggtggt agacgagctg     420
ggctgcagcc gccaacgggc cccttccagc aaacaggtga atggggtgca gaagcagaga     480
cggctagcag ccaacgccag ggagcggcgc aggatgcatg ggctgaacca cgccttcgac     540
cagctgcgca atgttatccc gtcgttcaac aacgacaaga agctgtccaa atatgagacc     600
ctgcagatgg cccaaatcta catcaacgcc ttgtccgagc tgctacaaac gcccagcgga     660
ggggaacagc caccgccgcc tccagcctcc tgcaaaagcg accaccacca ccttcgcacc     720
gcggcctcct atgaaggggg cgcgggcaac gcgaccgcag ctggggctca gcaggcttcc     780
ggagggagcc agcggccgac cccgcccggg agttgccgga ctcgcttctc agccccagct     840
tctgcgggag ggtactcggt gcagctggac gctctgcact tctcgacttt cgaggacagc     900
gccctgacag cgatgatggc gcaaaagaat ttgtctcctt ctctccccgg gagcatcttg     960
cagccagtgc aggaggaaaa cagcaaaact tcgcctcggt cccacagaag cgacggggaa    1020
ttttcccccc attcccatta cagtgactcg gatgaggcaa gttag                    1065

<210> SEQ ID NO 2
<211> LENGTH: 354
<212> TYPE: PRT
<213> ORGANISM: Homo sapiens

<400> SEQUENCE: 2

Met Ser Arg Leu Leu His Ala Glu Glu Trp Ala Glu Val Lys Glu Leu
 1               5                  10                  15
```

Gly Asp His His Arg Gln Pro Gln Pro His His Leu Pro Gln Pro Pro
             20                  25                  30

Pro Pro Pro Gln Pro Pro Ala Thr Leu Gln Ala Arg Glu His Pro Val
         35                  40                  45

Tyr Pro Pro Glu Leu Ser Leu Leu Asp Ser Thr Asp Pro Arg Ala Trp
 50                  55                  60

Leu Ala Pro Thr Leu Gln Gly Ile Cys Thr Ala Arg Ala Ala Gln Tyr
 65                  70                  75                  80

Leu Leu His Ser Pro Glu Leu Gly Ala Ser Glu Ala Ala Ala Pro Arg
                 85                  90                  95

Asp Glu Val Asp Gly Arg Gly Glu Leu Val Arg Arg Ser Ser Gly Gly
            100                 105                 110

Ala Ser Ser Ser Lys Ser Pro Gly Pro Val Lys Val Arg Glu Gln Leu
        115                 120                 125

Cys Lys Leu Lys Gly Gly Val Val Asp Glu Leu Gly Cys Ser Arg
    130                 135                 140

Gln Arg Ala Pro Ser Ser Lys Gln Val Asn Gly Val Gln Lys Gln Arg
145                 150                 155                 160

Arg Leu Ala Ala Asn Ala Arg Glu Arg Arg Met His Gly Leu Asn
                165                 170                 175

His Ala Phe Asp Gln Leu Arg Asn Val Ile Pro Ser Phe Asn Asn Asp
            180                 185                 190

Lys Lys Leu Ser Lys Tyr Glu Thr Leu Gln Met Ala Gln Ile Tyr Ile
        195                 200                 205

Asn Ala Leu Ser Glu Leu Leu Gln Thr Pro Ser Gly Gly Glu Gln Pro
210                 215                 220

Pro Pro Pro Ala Ser Cys Lys Ser Asp His His His Leu Arg Thr
225                 230                 235                 240

Ala Ala Ser Tyr Glu Gly Gly Ala Gly Asn Ala Thr Ala Ala Gly Ala
                245                 250                 255

Gln Gln Ala Ser Gly Gly Ser Gln Arg Pro Thr Pro Pro Gly Ser Cys
            260                 265                 270

Arg Thr Arg Phe Ser Ala Pro Ala Ser Ala Gly Gly Tyr Ser Val Gln
        275                 280                 285

Leu Asp Ala Leu His Phe Ser Thr Phe Glu Asp Ser Ala Leu Thr Ala
290                 295                 300

Met Met Ala Gln Lys Asn Leu Ser Pro Ser Leu Pro Gly Ser Ile Leu
305                 310                 315                 320

Gln Pro Val Gln Glu Glu Asn Ser Lys Thr Ser Pro Arg Ser His Arg
                325                 330                 335

Ser Asp Gly Glu Phe Ser Pro His Ser His Tyr Ser Asp Ser Asp Glu
            340                 345                 350

Ala Ser

<210> SEQ ID NO 3
<211> LENGTH: 2144
<212> TYPE: DNA
<213> ORGANISM: Mus musculus

<400> SEQUENCE: 3
tcgacccacg cgtccgccca cgcgtccgga tctccgagtg agaggggag ggtcagagga      60 ggaaggaaaa aaaaatcaga ccttgcagaa gagactagga aggttttgt tgttgttgtt     120 cggggcttat ccccttcgtt gaactgggtt gccagcacct cctctaacac ggcacctccg    180

-continued

| | |
|---|---|
| agccattgca gtgcgatgtc ccgcctgctg catgcagaag agtgggctga ggtaaaagag | 240 |
| ttggggggacc accatcgcca tccccagccg caccacgtcc cgccgctgac gccacagcca | 300 |
| cctgctaccc tgcaggcgag agaccttccc gtctacccgg cagaactgtc cctcctggat | 360 |
| agcaccgacc cacgcgcctg gctgactccc actttgcagg gcctctgcac ggcacgcgcc | 420 |
| gcccagtatc tgctgcattc tcccgagctg ggtgcctccg aggccgcggc gccccgggac | 480 |
| gaggctgaca gccagggtga gctggtaagg agaagcggct gtggcggcct cagcaagagc | 540 |
| cccgggcccg tcaaagtacg ggaacagctg tgcaagctga agggtggggt tgtagtggac | 600 |
| gagcttggct gcagccgcca gcgagcccct tccagcaaac aggtgaatgg ggtacagaag | 660 |
| caaaggaggc tggcagcaaa cgcaagggaa cggcgcagga tgcacgggct gaaccacgcc | 720 |
| ttcgaccagc tgcgcaacgt tatcccgtcc ttcaacaacg acaagaagct gtccaaatat | 780 |
| gagaccctac agatggccca gatctacatc aacgctctgt cggagttgct gcagactccc | 840 |
| aatgtcggag agcaaccgcc gccgcccaca gcttcctgca aaaatgacca ccatcacctt | 900 |
| cgcaccgcct cctcctatga aggaggtgcg ggcgcctctg cggtagctgg ggctcagcca | 960 |
| gccccgggag ggggcccgag acctaccccg cccgggcctt gccggactcg cttctcaggc | 1020 |
| ccagcttcct ctgggggtta ctcggtgcag ctggacgctt tgcacttccc agccttcgag | 1080 |
| gacagggccc taacagcgat gatggcacag aaggacctgt cgccttcgct gcccggggggc | 1140 |
| atcctgcagc ctgtacagga ggacaacagc aaaacatctc ccagatccca cagaagtgac | 1200 |
| ggagagttt cccccccactc tcattacagt gactctgatg aggccagtta ggaaggcaac | 1260 |
| agctccctga aaactgagac aaccaaatgc ccttcctagc gcgcgggaag ccccgtgaca | 1320 |
| aatatccctg caccctttaa ttttggtct gtggtgatcg ttgttagcaa cgacttgact | 1380 |
| tcggacggct gcagctcttc caatcccctt cctcctacct tctccttcct ctgtatgtag | 1440 |
| atactgtatc attatatgta cctttacgtg gcatcgtttc atggtccatg ctgccaatat | 1500 |
| gctgctaaaa tgtcgtatct ctgcctctgg tctgggtttc acttatttta taccttggga | 1560 |
| gttcatcctt gcgtgttgcg ctcactcaca aataagggag ttagtcaatg aagttgtttc | 1620 |
| cccaactgct tgagacccgc attgggtact ttactgaaca cggactattg tgttgttaaa | 1680 |
| atgcagggc agataagagt atctgtagag cttagacacc aagtgtgtcc agcagtgtgt | 1740 |
| ctagcggacc cagaatacac gcacttcatc actggccgct cgccgccctt gaagaaactc | 1800 |
| aactgccaat gcagagcaac ttttgatttt aaaaacagcc actcataatc attaaactct | 1860 |
| ttgcaaatgt ttgttttgc aaatgaaaat taaaaaaaa catgtagtgt caaaggcatt | 1920 |
| tggtcaattt tattttgctt tgttaacatt agaaagtta tttattattg cgtatttgga | 1980 |
| cccatttcta cttaattgcc ttttttttac attttctact cgagatcgtt ttattttgat | 2040 |
| ttagcaaatc cagttgccat tgctttatgt atgtatgctc ttttacaaat gataaaataa | 2100 |
| actcggaaaa aaaaaaaaa aaaaaaaaa aaaaaaaaa aaaa | 2144 |

<210> SEQ ID NO 4
<211> LENGTH: 235
<212> TYPE: PRT
<213> ORGANISM: Mus musculus

<400> SEQUENCE: 4

Met Ser Arg Leu Leu His Ala Glu Glu Trp Ala Glu Val Lys Glu Leu
1               5                   10                  15

Gly Asp His His Arg His Pro Gln Pro His His Val Pro Pro Leu Thr
            20                  25                  30

```
Pro Gln Pro Ala Thr Leu Gln Ala Arg Asp Leu Leu Val Arg Arg
        35                  40                  45

Ser Gly Cys Gly Gly Leu Ser Lys Ser Pro Gly Pro Val Lys Val Arg
 50                  55                  60

Glu Gln Leu Cys Lys Leu Lys Gly Gly Val Val Val Asp Glu Leu Gly
 65                  70                  75                  80

Cys Ser Arg Gln Arg Ala Pro Ser Ser Lys Gln Val Asn Gly Val Gln
                 85                  90                  95

Lys Gln Arg Arg Leu Ala Ala Asn Ala Arg Glu Arg Arg Arg Met His
                100                 105                 110

Gly Leu Asn His Ala Phe Asp Gln Leu Arg Asn Val Ile Pro Ser Phe
                115                 120                 125

Asn Asn Asp Lys Lys Leu Ser Lys Tyr Glu Thr Leu Gln Met Ala Gln
130                 135                 140

Ile Tyr Ile Asn Ala Leu Ser Glu Leu Leu Gln Thr Pro Asn Val Gly
145                 150                 155                 160

Ala Ser Ser Gly Gly Tyr Ser Val Gln Leu Asp Ala Leu His Phe Pro
                165                 170                 175

Ala Phe Glu Asp Arg Ala Leu Thr Ala Met Met Ala Gln Lys Asp Leu
                180                 185                 190

Ser Pro Ser Leu Pro Gly Gly Ile Leu Gln Pro Val Gln Glu Asp Asn
                195                 200                 205

Ser Lys Thr Ser Pro Arg Ser His Arg Ser Asp Gly Glu Phe Ser Pro
                210                 215                 220

His Ser His Tyr Ser Asp Ser Asp Glu Ala Ser
225                 230                 235

<210> SEQ ID NO 5
<211> LENGTH: 717
<212> TYPE: DNA
<213> ORGANISM: Gallus gallus

<400> SEQUENCE: 5
atggccccag aggtagcga gtgttgttgc agtgatgccg cgcacatcac ttggaggcag      60
tgggagtaca cgcacgagaa ccaactgtgc gtggcaggaa ctgtcagcag gatgaggccc     120
aggacgtggg tctgcaccgg atctttgtgg gaccaggaag cgggaattac tttgatgggc     180
ccccaaatac ccaaagtgga tgaggcagga gtgatgaccc acccggcaag gtcgctttgc     240
agcactgggg cacatccgtg tcccggggtg gtcgtgctgc ccacgggtgg ataggcag      300 ccttcaaaga agctctccaa gtacgagacg ctgcagatgg cgcaaatcta catcagcgcc     360
ctcgccgagc ttctgcacgg gccgcccgcg ccccccgagc cgcccgccaa ggccgagctc     420
cgcgggggcc ccttcgagcc tcccccgccg ccccctcctc cgccgccccg cgcctcgccc     480
cccgcgcccg ccaggactcg cttccccccg gcggcggccg cgggcggttt cgcggcgctt     540
ctcgagccgc tgcgcttccc ttctttcccg gcgcagaaag cgccttctcc cgcgctgctc     600
ctggggccgc ccgcgccgca gcagcccgag aggagcaaag cgtcgccgcg ctctcaccgc     660
agcgacgggg agttctcgcc gcgctcccac tacagtgact cggacgaggc cagctag        717

<210> SEQ ID NO 6
<211> LENGTH: 238
<212> TYPE: PRT
<213> ORGANISM: Gallus gallus

<400> SEQUENCE: 6
```

```
Met Ala Pro Gly Gly Ser Glu Cys Cys Cys Ser Asp Ala Ala His Ile
 1               5                  10                  15

Thr Trp Arg Gln Trp Glu Tyr Thr His Glu Asn Gln Leu Cys Val Ala
            20                  25                  30

Gly Thr Val Ser Arg Met Arg Pro Arg Thr Trp Val Cys Thr Gly Ser
        35                  40                  45

Leu Trp Asp Gln Glu Ala Gly Ile Thr Leu Met Gly Pro Gln Ile Pro
 50                  55                  60

Lys Val Asp Glu Ala Gly Val Met Thr His Pro Ala Arg Ser Leu Cys
65                  70                  75                  80

Ser Thr Gly Ala His Pro Cys Pro Gly Val Val Leu Pro Thr Gly
                85                  90                  95

Gly Ile Gly Gln Pro Ser Lys Lys Leu Ser Lys Tyr Glu Thr Leu Gln
            100                 105                 110

Met Ala Gln Ile Tyr Ile Ser Ala Leu Ala Glu Leu Leu His Gly Pro
        115                 120                 125

Pro Ala Pro Pro Glu Pro Ala Lys Ala Glu Leu Arg Gly Ala Pro
130                 135                 140

Phe Glu Pro Pro Pro Pro Pro Pro Pro Arg Ala Ser Pro
145                 150                 155                 160

Pro Ala Pro Ala Arg Thr Arg Phe Pro Ala Ala Ala Gly Gly
            165                 170                 175

Phe Ala Ala Leu Leu Glu Pro Leu Arg Phe Pro Ser Phe Pro Ala Gln
                180                 185                 190

Lys Ala Pro Ser Pro Ala Leu Leu Leu Gly Pro Pro Ala Pro Gln Gln
            195                 200                 205

Pro Glu Arg Ser Lys Ala Ser Pro Arg Ser His Arg Ser Asp Gly Glu
210                 215                 220

Phe Ser Pro Arg Ser His Tyr Ser Asp Ser Asp Glu Ala Ser
225                 230                 235

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
atggctggac acctggcttc ag                                          22

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
ttaaccccaa agctccaggt tc                                          22

<210> SEQ ID NO 9
<211> LENGTH: 25
<212> TYPE: DNA
<213> ORGANISM: Artificial Sequence
<220> FEATURE:
<223> OTHER INFORMATION: Primer

<400> SEQUENCE: 9
```

-continued

```
ccatgaccta tactcaggct tcagg                                          25

<210> SEQ ID NO 10
<211> LENGTH: 26
<212> TYPE: DNA
<213> ORGANISM: Artificial Sequence
<220> FEATURE:
<223> OTHER INFORMATION: Primer

<400> SEQUENCE: 10
gaagctccat atccctgggt ggaaag                                         26

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
cacccgggcc tcaacgctca cg                                             22

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
tccccttctc cagttcgcag tcca                                           24

<210> SEQ ID NO 13
<211> LENGTH: 23
<212> TYPE: DNA
<213> ORGANISM: Artificial Sequence
<220> FEATURE:
<223> OTHER INFORMATION: Primer

<400> SEQUENCE: 13
ccaaagtggt ggacaagatt gcc                                            23

<210> SEQ ID NO 14
<211> LENGTH: 23
<212> TYPE: DNA
<213> ORGANISM: Artificial Sequence
<220> FEATURE:
<223> OTHER INFORMATION: Primer

<400> SEQUENCE: 14
ggataggaag gacgctcaaa gac                                            23

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
agactttaac caagggcggt                                                20

<210> SEQ ID NO 16
<211> LENGTH: 20
<212> TYPE: DNA
```

```
<213> ORGANISM: Artificial Sequence
<220> FEATURE:
<223> OTHER INFORMATION: Primer

<400> SEQUENCE: 16
tagccaggtt gcgaagaact                                                    20

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
aacagagatt ggaaggccgc tggc                                               24

<210> SEQ ID NO 18
<211> LENGTH: 23
<212> TYPE: DNA
<213> ORGANISM: Artificial Sequence
<220> FEATURE:
<223> OTHER INFORMATION: Primer

<400> SEQUENCE: 18
cttcagaaag gctgtcacag gag                                                23

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
atggagactg acgcgcccca g                                                  21

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
atcttcttcg tccgagtgac                                                    20

<210> SEQ ID NO 21
<211> LENGTH: 18
<212> TYPE: DNA
<213> ORGANISM: Artificial Sequence
<220> FEATURE:
<223> OTHER INFORMATION: Primer

<400> SEQUENCE: 21
cctccgacgg caggagtc                                                      18

<210> SEQ ID NO 22
<211> LENGTH: 21
<212> TYPE: DNA
<213> ORGANISM: Artificial Sequence
<220> FEATURE:
<223> OTHER INFORMATION: Primer

<400> SEQUENCE: 22
accgtagccc tgacggagtt t                                                  21
```

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
agatctacat caacgctctg tc                                              22

<210> SEQ ID NO 24
<211> LENGTH: 22
<212> TYPE: DNA
<213> ORGANISM: Artificial Sequence
<220> FEATURE:
<223> OTHER INFORMATION: Primer

<400> SEQUENCE: 24
actggcctca tcagagtcac tg                                              22

<210> SEQ ID NO 25
<211> LENGTH: 17
<212> TYPE: DNA
<213> ORGANISM: Artificial Sequence
<220> FEATURE:
<223> OTHER INFORMATION: Primer

<400> SEQUENCE: 25
tggtgtcgtc ggggaac                                                    17

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
aaggccgacc tccaaacctc                                                 20

<210> SEQ ID NO 27
<211> LENGTH: 23
<212> TYPE: DNA
<213> ORGANISM: Artificial Sequence
<220> FEATURE:
<223> OTHER INFORMATION: Primer

<400> SEQUENCE: 27
acgggctgaa cgcggcgctg gac                                             23

<210> SEQ ID NO 28
<211> LENGTH: 23
<212> TYPE: DNA
<213> ORGANISM: Artificial Sequence
<220> FEATURE:
<223> OTHER INFORMATION: Primer

<400> SEQUENCE: 28
tgaaagagaa gttgccattg atg                                             23

<210> SEQ ID NO 29
<211> LENGTH: 19
<212> TYPE: DNA
<213> ORGANISM: Artificial Sequence
<220> FEATURE:

<223> OTHER INFORMATION: Primer

<400> SEQUENCE: 29
gccatgcgcc gagtttgtc                                                  19

<210> SEQ ID NO 30
<211> LENGTH: 18
<212> TYPE: DNA
<213> ORGANISM: Artificial Sequence
<220> FEATURE:
<223> OTHER INFORMATION: Primer

<400> SEQUENCE: 30
atggcgccta gatgatgc                                                   18

<210> SEQ ID NO 31
<211> LENGTH: 22
<212> TYPE: DNA
<213> ORGANISM: Artificial Sequence
<220> FEATURE:
<223> OTHER INFORMATION: Primer

<400> SEQUENCE: 31
cagcctgagt caccgcagcc tc                                              22

<210> SEQ ID NO 32
<211> LENGTH: 23
<212> TYPE: DNA
<213> ORGANISM: Artificial Sequence
<220> FEATURE:
<223> OTHER INFORMATION: Primer

<400> SEQUENCE: 32
tgacctgtcg ctgccagggc gcg                                             23

<210> SEQ ID NO 33
<211> LENGTH: 23
<212> TYPE: DNA
<213> ORGANISM: Artificial Sequence
<220> FEATURE:
<223> OTHER INFORMATION: Primer

<400> SEQUENCE: 33
ctccctctac atcgctctgt tcg                                             23

<210> SEQ ID NO 34
<211> LENGTH: 25
<212> TYPE: DNA
<213> ORGANISM: Artificial Sequence
<220> FEATURE:
<223> OTHER INFORMATION: Primer

<400> SEQUENCE: 34
aagcacctgc tcctgctcgt ccacg                                           25

<210> SEQ ID NO 35
<211> LENGTH: 21
<212> TYPE: DNA
<213> ORGANISM: Artificial Sequence
<220> FEATURE:
<223> OTHER INFORMATION: Primer

<400> SEQUENCE: 35
ggccaacccc aaaaagtcgt g                                               21

```
<210> SEQ ID NO 36
<211> LENGTH: 22
<212> TYPE: DNA
<213> ORGANISM: Artificial Sequence
<220> FEATURE:
<223> OTHER INFORMATION: Primer

<400> SEQUENCE: 36
gagagctggg gtgcgtgtag ga                                          22

<210> SEQ ID NO 37
<211> LENGTH: 24
<212> TYPE: DNA
<213> ORGANISM: Artificial Sequence
<220> FEATURE:
<223> OTHER INFORMATION: Primer

<400> SEQUENCE: 37
ggcggcgcag ctccacaacc agta                                        24

<210> SEQ ID NO 38
<211> LENGTH: 24
<212> TYPE: DNA
<213> ORGANISM: Artificial Sequence
<220> FEATURE:
<223> OTHER INFORMATION: Primer

<400> SEQUENCE: 38
ttgccacagc ccgggaaagg acag                                        24

<210> SEQ ID NO 39
<211> LENGTH: 19
<212> TYPE: DNA
<213> ORGANISM: Artificial Sequence
<220> FEATURE:
<223> OTHER INFORMATION: Primer

<400> SEQUENCE: 39
ttgccccttc ccctttat                                               19

<210> SEQ ID NO 40
<211> LENGTH: 17
<212> TYPE: DNA
<213> ORGANISM: Artificial Sequence
<220> FEATURE:
<223> OTHER INFORMATION: Primer

<400> SEQUENCE: 40
cgcttgctcg ctctcgt                                                17

<210> SEQ ID NO 41
<211> LENGTH: 17
<212> TYPE: DNA
<213> ORGANISM: Artificial Sequence
<220> FEATURE:
<223> OTHER INFORMATION: Primer

<400> SEQUENCE: 41
acccgcatcc cagtcat                                                17

<210> SEQ ID NO 42
<211> LENGTH: 18
<212> TYPE: DNA
<213> ORGANISM: Artificial Sequence
<220> FEATURE:
<223> OTHER INFORMATION: Primer
```

<400> SEQUENCE: 42
tcccggtgta caaagtgc                                            18

<210> SEQ ID NO 43
<211> LENGTH: 22
<212> TYPE: DNA
<213> ORGANISM: Artificial Sequence
<220> FEATURE:
<223> OTHER INFORMATION: Primer

<400> SEQUENCE: 43
ctggagcgga tggacgccag ac                                       22

<210> SEQ ID NO 44
<211> LENGTH: 21
<212> TYPE: DNA
<213> ORGANISM: Artificial Sequence
<220> FEATURE:
<223> OTHER INFORMATION: Primer

<400> SEQUENCE: 44
cgtctgctcc acagtgccag c                                        21

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
gtccttccca catgggagtt                                          20

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
gtttccacct tgacctcggt                                          20

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
agagatgtgg gatgcaggac                                          20

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
cacacaggga acttcaccct                                          20

<210> SEQ ID NO 49
<211> LENGTH: 18

```
<212> TYPE: DNA
<213> ORGANISM: Artificial Sequence
<220> FEATURE:
<223> OTHER INFORMATION: Primer

<400> SEQUENCE: 49
gtcgtgggcc ttgtggcc                                                  18

<210> SEQ ID NO 50
<211> LENGTH: 19
<212> TYPE: DNA
<213> ORGANISM: Artificial Sequence
<220> FEATURE:
<223> OTHER INFORMATION: Primer

<400> SEQUENCE: 50
ctgtgagttc acactgggg                                                 19

<210> SEQ ID NO 51
<211> LENGTH: 18
<212> TYPE: DNA
<213> ORGANISM: Artificial Sequence
<220> FEATURE:
<223> OTHER INFORMATION: Primer

<400> SEQUENCE: 51
gccaaccgtg tgctgctg                                                  18

<210> SEQ ID NO 52
<211> LENGTH: 19
<212> TYPE: DNA
<213> ORGANISM: Artificial Sequence
<220> FEATURE:
<223> OTHER INFORMATION: Primer

<400> SEQUENCE: 52
acgtcgagac tgggcaagg                                                 19

<210> SEQ ID NO 53
<211> LENGTH: 17
<212> TYPE: DNA
<213> ORGANISM: Artificial Sequence
<220> FEATURE:
<223> OTHER INFORMATION: Primer

<400> SEQUENCE: 53
ccagcacagc ggtccag                                                   17

<210> SEQ ID NO 54
<211> LENGTH: 21
<212> TYPE: DNA
<213> ORGANISM: Artificial Sequence
<220> FEATURE:
<223> OTHER INFORMATION: Primer

<400> SEQUENCE: 54
ggggcacggt tgtccttgta g                                              21

<210> SEQ ID NO 55
<211> LENGTH: 22
<212> TYPE: DNA
<213> ORGANISM: Artificial Sequence
<220> FEATURE:
<223> OTHER INFORMATION: Primer

<400> SEQUENCE: 55
```
cggaaccaga gataggacct ac                                              22

<210> SEQ ID NO 56
<211> LENGTH: 22
<212> TYPE: DNA
<213> ORGANISM: Artificial Sequence
<220> FEATURE:
<223> OTHER INFORMATION: Primer

<400> SEQUENCE: 56
ctaagcacgg gttgcctcat cc                                              22

<210> SEQ ID NO 57
<211> LENGTH: 18
<212> TYPE: DNA
<213> ORGANISM: Artificial Sequence
<220> FEATURE:
<223> OTHER INFORMATION: Primer

<400> SEQUENCE: 57
aacgggaagc ccatcacc                                                   18

<210> SEQ ID NO 58
<211> LENGTH: 18
<212> TYPE: DNA
<213> ORGANISM: Artificial Sequence
<220> FEATURE:
<223> OTHER INFORMATION: Primer

<400> SEQUENCE: 58
cagccttggc agcaccag                                                   18

<210> SEQ ID NO 59
<211> LENGTH: 2013
<212> TYPE: DNA
<213> ORGANISM: Artificial Sequence
<220> FEATURE:
<223> OTHER INFORMATION: Synthetic construct

<400> SEQUENCE: 59
atgtccaatt tactgaccgt acaccaaaat ttgcctgcat taccggtcga tgcaacgagt       60
gatgaggttc gcaagaacct gatggacatg ttcagggatc gccaggcgtt ttctgagcat      120
acctggaaaa tgcttctgtc cgtttgccgg tcgtgggcgg catggtgcaa gttgaataac      180
cggaaatggt tcccgcagaa acctgaagat gttcgcgatt atcttctata tcttcaggcg      240
cgcggtctgg cagtaaaaac tatccagcaa catttgggcc agctaaacat gcttcatcgt      300
cggtccgggc tgccacgacc aagtgacagc aatgctgttt cactggttat gcggcggatc      360
cgaaaagaaa acgttgatgc cggtgaacgt gcaaaacagg ctctagcgtt cgaacgcact      420
gatttcgacc aggttcgttc actcatggaa aatagcgatc gctgccagga tatacgtaat      480
ctggcatttc tggggattgc ttataacacc ctgttacgta tagccgaaat tgccaggatc      540
agggttaaag atatctcacg tactgacggt gggagaatgt taatccatat tggcagaacg      600
aaaacgctgg ttagcaccgc aggtgtagag aaggcactta gcctggggt aactaaactg      660
gtcgagcgat ggatttccgt ctctggtgta gctgatgatc cgaataacta cctgttttgc      720
cgggtcagaa aaaatggtgt tgccgcgcca tctgccacca gccagctatc aactcgcgcc      780
ctggaaggga ttttttgaagc aactcatcga ttgatttacg cgctaaggat gactctggt      840
cagagatacc tggcctggtc tggacacagt gcccgtgtcg gagccgcgcg agatatggcc      900
cgcgctggag tttcaatacc ggagatcatg caagctggtg gctggaccaa tgtaaatatt      960

-continued

```
gtcatgaact atatccgtaa cctggatagt gaaacagggg caatggtgcg cctgctggaa    1020
gatggggatc aggctggtgc catgggcgat ccacgaaatg aaatgggtgc ttcaggagac    1080
atgagggctg ccaacctttg gccaagccct cttgtgatta agcacactaa gaagaatagc    1140
cctgccttgt ccttgacagc tgaccagatg gtcagtgcct tgttggatgc tgaaccgccc    1200
atgatctatt ctgaatatga tccttctaga cccttcagtg aagcctcaat gatgggctta    1260
ttgaccaacc tagcagatag ggagctggtt catatgatca actgggcaaa gagagtgcca    1320
ggctttgggg acttgaatct ccatgatcag gtccaccttc tcgagtgtgc ctggctggag    1380
attctgatga ttggtctcgt ctggcgctcc atgaacacc cggggaagct cctgtttgct     1440
cctaacttgc tcctggacag gaatcaaggt aaatgtgtgg aaggcatggt ggagatcttt    1500
gacatgttgc ttgctacgtc aagtcggttc cgcatgatga acctgcaggg tgaagagttt    1560
gtgtgcctca aatccatcat tttgcttaat tccggagtgt acacgtttct gtccagcacc    1620
ttgaagtctc tggaagagaa ggaccacatc caccgtgtcc tggacaagat cacagacact    1680
ttgatccacc tgatggccaa agctggcctg actctgcagc agcagcatcg ccgcctagct    1740
cagctccttc tcattctttc ccatatccgg cacatgagta acaaacgcat ggagcatctc    1800
tacaacatga aatgcaagaa cgtggtaccc ctctatgacc tgctcctgga gatgttggat    1860
gcccaccgcc ttcatgcccc agccagtcgc atgggagtgc ccccagagga gcccagccag    1920
acccagctgg ccaccaccag ctccacttca gcacattcct tacaaaccta ctacataccc    1980
ccggaagcag agggcttccc caacacgatc tga                                 2013
```